US010166116B2

(12) United States Patent
Janowski

(10) Patent No.: US 10,166,116 B2
(45) Date of Patent: Jan. 1, 2019

(54) HELICAL LOCK SPACER, INSTRUMENTS AND METHODS

(71) Applicant: Brian Patrick Janowski, Marquette, MI (US)

(72) Inventor: Brian Patrick Janowski, Marquette, MI (US)

( * ) Notice: Subject to any disclaimer, the term of this patent is extended or adjusted under 35 U.S.C. 154(b) by 207 days.

(21) Appl. No.: 15/367,540

(22) Filed: Dec. 2, 2016

(65) Prior Publication Data

US 2017/0156879 A1 Jun. 8, 2017

Related U.S. Application Data

(60) Provisional application No. 62/262,129, filed on Dec. 2, 2015.

(51) Int. Cl.
*A61F 2/46* (2006.01)
*A61F 2/44* (2006.01)
*A61F 2/30* (2006.01)

(52) U.S. Cl.
CPC .......... *A61F 2/447* (2013.01); *A61F 2/30749* (2013.01); *A61F 2/4455* (2013.01); *A61F 2/4611* (2013.01); *A61F 2002/3082* (2013.01); *A61F 2002/30092* (2013.01); *A61F 2002/3093* (2013.01); *A61F 2002/30289* (2013.01); *A61F 2002/30822* (2013.01); *A61F 2002/30904* (2013.01); *A61F 2002/4475* (2013.01); *A61F 2002/4623* (2013.01); *A61F 2002/4627* (2013.01); *A61F 2310/00017* (2013.01); *A61F 2310/00023* (2013.01); *A61F 2310/00029* (2013.01); *A61F 2310/00071* (2013.01)

(58) Field of Classification Search
CPC .... A61F 2/3079; A61F 2/4455; A61F 2/4465; A61F 2/447; A61F 2/4611; A61F 2002/30822; A61F 2002/4627
See application file for complete search history.

(56) References Cited

U.S. PATENT DOCUMENTS

| 6,159,245 | A | 12/2000 | Meriwether et al. |
|---|---|---|---|
| 6,296,656 | B1 | 10/2001 | Bolduc et al. |
| 6,689,168 | B2 | 2/2004 | Lieberman |
| 7,297,162 | B2 | 11/2007 | Mujwid |
| 8,197,513 | B2 | 6/2012 | Fisher et al. |
| 8,460,385 | B1 | 6/2013 | Wensel |
| 8,900,310 | B2 | 12/2014 | Carlson et al. |

(Continued)

*Primary Examiner* — Nicholas Woodall
(74) *Attorney, Agent, or Firm* — Device Patent LLC

(57) ABSTRACT

Disclosed are bone spacing implants for bone fusion with an open helix locking system and insertion instrumentation for implanting a spacer and fixating with a helix lock without removal of instrumentation between steps. Implanting methods comprise the steps of: positioning a coil driver over an elongate shaft portion of a bone spacer inserter; loading a helical lock implant on a distal end of an elongate shaft portion wherein an elongate shaft portion occupies a central core space of the helical lock; positioning and fixing a selected bone spacer implant to the bone spacer inserter instrument; advancing the bone spacer and helical lock instrumentation assembly into an intervertebral space; advancing through rotation a coil driver transmitting torsional forces against a butt surface of a helix lock until the helix lock is fully threaded into adjacent bone and the bone spacer.

20 Claims, 17 Drawing Sheets

(56) References Cited

U.S. PATENT DOCUMENTS

| | | | |
|---|---|---|---|
| 9,107,760 B2 | 8/2015 | Walters | |
| 9,456,904 B2 * | 10/2016 | Landry | A61F 2/4455 |
| 9,750,616 B2 | 9/2017 | Blain et al. | |
| 2002/0177898 A1 | 11/2002 | Crozet | |
| 2005/0143733 A1 * | 6/2005 | Petit | A61F 2/4425 |
| | | | 606/60 |
| 2009/0164020 A1 | 6/2009 | Janowski et al. | |
| 2011/0166660 A1 * | 7/2011 | Laurence | A61F 2/44 |
| | | | 623/17.16 |
| 2012/0179163 A1 * | 7/2012 | Housman | A61B 17/0401 |
| | | | 606/104 |
| 2012/0232597 A1 | 9/2012 | Saidha et al. | |
| 2012/0277868 A1 | 11/2012 | Walters | |
| 2014/0052260 A1 | 2/2014 | McKenny et al. | |
| 2014/0114418 A1 | 4/2014 | Landry et al. | |
| 2014/0180417 A1 | 6/2014 | Bergey | |
| 2015/0066145 A1 | 3/2015 | Rogers et al. | |

* cited by examiner

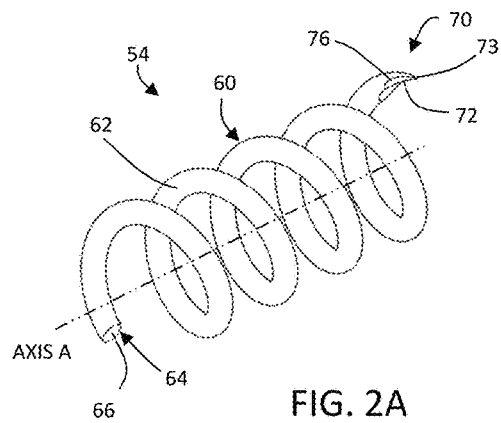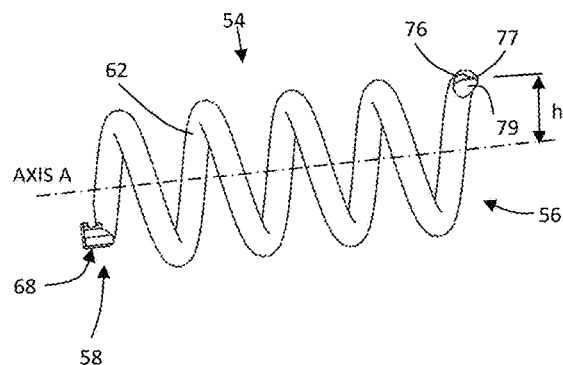
FIG. 2A  FIG. 2B
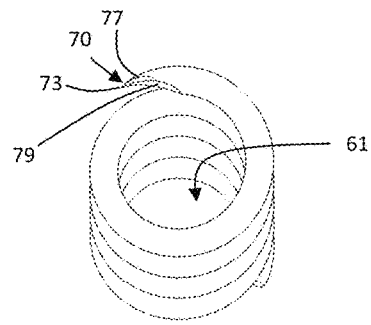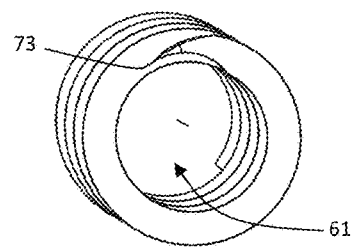
FIG. 2C  FIG. 2D
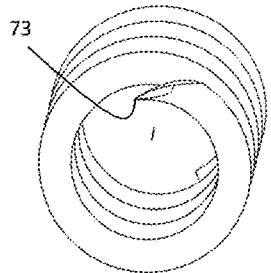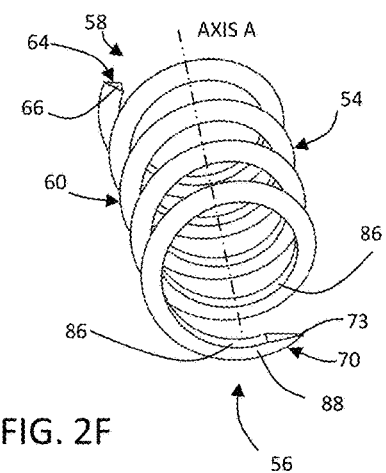
FIG. 2E  FIG. 2F

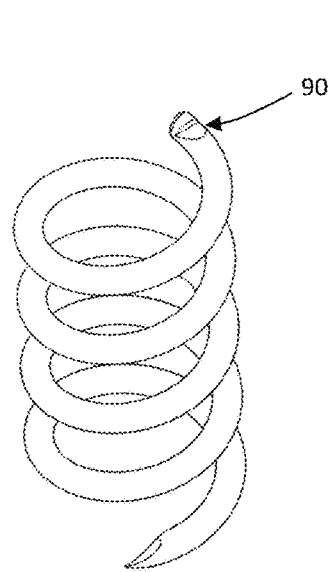
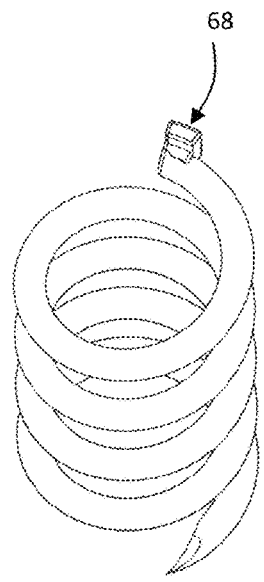
FIG. 2I
FIG. 2K
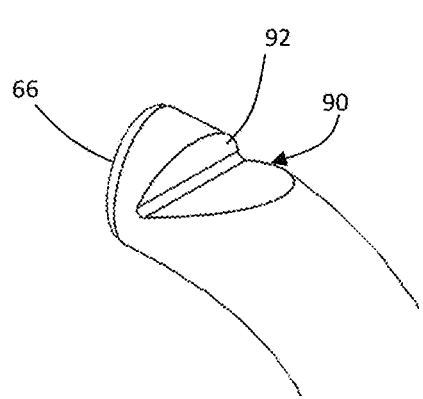
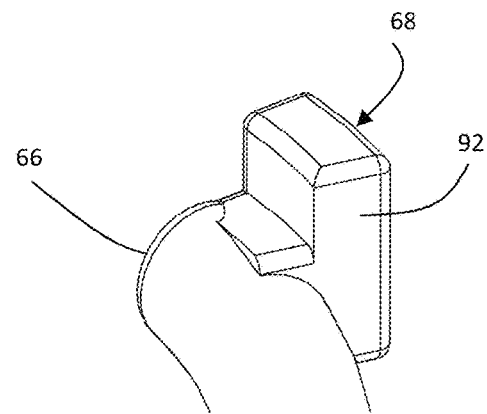
FIG. 2J
FIG. 2L

HELICAL LOCK SPACER, INSTRUMENTS AND METHODS

This application is a U.S. Non-Provisional Patent application claiming benefit of priority to U.S. Provisional Patent Application No. 62/262,129 filed Dec. 2, 2015, the entire disclosure of which is hereby incorporated by reference and relied upon.

BACKGROUND OF THE INVENTION

Field of the Invention

The invention relates generally to bone spacers utilizing a helical lock and specialized surgical instruments and methods for insertion thereof.

Description of Related Art

The prior art illustrates a variety of approaches to secure a spacer between two bone segments. These bone segments are typically vertebral bodies and the spacer is typically an intervertebral spacer. Crozet for example (US 2002/0177898) discloses a spacer and screw like members having a helical thread that engages the surface of the bone to fix the spacer in position. Landry (US2014/0114418) uses a similar open helical device to accomplish a similar feat to cause fixation of a facet joint. Carlson (U.S. Pat. No. 8,900,310) also combines a rotating helical member within a spacer as does Laurence (US 2011/0166660) who uses an open helix device and discloses an open helix insertion tool. McKenny (US2014/0052260) discloses an spacer design utilizing a first curved path blade that is inserted through an aperture of the spacer. Mujwid (U.S. Pat. No. 7,297,162) discloses an expandable spring like implant that bulges upon compression of the spring. Lieberman (U.S. Pat. No. 6,689,168) discloses an open helix device for advancing into a pair of adjacent vertebral bodies. Bolduc (U.S. Pat. No. 6,296,656) discloses an array of open helix designs and an applicator device for insertion.

A need remains for robust intervertebral spacers that are inserted using a minimally invasive approach requiring only a minimal incision to gain access to the intervertebral space along a single surgical axis. In addition, a need remains for spacers that include a fixation mechanism that not only holds the spacer in a pre-determined position between bone portions but also secures a bone portion, or an endplate in the case of a vertebral body, to the entire length of the corresponding face of the spacer without liftoff or gapping therebetween with skeletal movement. A need remains for spacer fixation systems that can be applied along a single surgical axis and do not require off angle insertion or tightening of fixation components. A need remains for spacer fixation systems that may be easily removed and adjusted once implanted if the need arises. A need remains for spacer and spacer fixation systems that can be inserted and deployed without a continual insertion and removal of multiple instruments. A need remains for spacer fixation systems which have a minimal profile to minimize disruption of the bone endplate and don't require pre-drilling. A need remains for spacer insertion instruments that simultaneously control both the spacer and the spacer fixation providing precise placement of not only the spacer but also simultaneous placement of the spacer fixator.

SUMMARY OF THE INVENTION

Novel bone spacers with fixation systems and methods are disclosed herein that address the short comings of the prior art devices. The spacers may assume a variety of forms as needed for the desired surgical approach. Although the spacer forms illustrated herein are intended for use in lateral lumbar surgical approaches, the spacers and their fixation system and instruments for insertion may be adapted for use using an anterior, antero-lateral, posterior, direct lateral, or transforaminal approach to the spine or other areas of the body such as sacral-iliac fusion. The spacer and helical lock may be formed from a wide variety of biocompatible materials not limited to titanium, titanium alloys, PAEK, PEEK, PDLA, PPLA, nitinol, stainless steel, cobalt-chrome, and allografts. The implants may also be coated with various surface coatings known in the art to improve bone growth or osteo-integration.

In one form, a bone spacer is configured for a lateral surgical approach.

In one form a bone spacer comprises a spacer body which may include a leading end, a trailing end, an upper surface, a lower surface, a leading surface, a trailing surface.

In one form, a bone spacer is configured with teeth disposed on one or more of an upper bone facing surface and a lower bone facing surface for engagement bone.

In one form, an upper bone facing surface and a lower bone facing surface may be generally parallel (0 degrees) or be angled at up to 12 degrees or more to fit within a space between the bones where it will reside.

In one form, one or more of an upper bone facing surface and lower bone facing surface may be curved to match adjacent bone.

In one form, one or more of an upper bone facing surface and lower bone facing surface has a general curvature of a spinal endplate.

In one form, a spacer wall encircles a spacer and is formed from a spacer body.

In one form, a spacer body may comprise one or more open and closed helical guides to guide a helical lock to predetermined positions and to minimize distortion of a helical lock as it is driven through bone.

In one form, a bone spacer comprises a plurality of helical guides spaced along a central axis of the bone spacer.

In one form, at least one closed helical guide is positioned near a distal end of a bone spacer.

In one form, at least one open helical guide is positioned near a distal end of a bone spacer.

In one form, at least one closed helical guide is positioned near a middle section of a bone spacer.

In one form, at least one open helical guide is positioned near a middle section of a bone spacer.

In one form, a spacer is manufactured from 3D printing or similar rapid prototyping methods to accommodate a specified shape and position of a helical guide which may be difficult or expensive to machine by traditional methods.

In one form, a spacer body includes a first helical guide for guiding a lead end and tip of a helical lock thereby making a starter hole at a predetermined location in a bone to assist with proper alignment of the spacer within the bone space.

In one form, a first helical guide aligns a helical path between an insertion instrument and bone spacer to provide a continuous guide pathway for a helical lock.

In one form, a portion of an inserter instrument includes a helical path for holding a helical lock in a predetermined position in preparation for insertion.

In one form, a helical path on an inserter instrument and a first helical guide on a spacer form a continuous guide path for inserting a helical lock at a pre-determined location within a bone.

In one form, a bone spacer includes a tip pocket for seating a cutting tip of a helix lock within a body of a spacer to provide structural support for the tip.

In one form, a bone spacer includes a tip pocket to serve as a stop indicating the helix lock is fully engaged as the spacer changes from a pre-lock to a fully locked or operative configuration.

In one form, a tip pocket is in the form of a depression within a spacer body.

In one form, a spacer lock on a trailing end of a spacer provides for spacer control by surgical instruments.

In one form, a spacer lock comprises a lock aperture which may further comprise threads.

In one form, a spacer lock comprises fixation features such as notches for use by an attached insertion instrument to provide directional control over a bone spacer.

In one form, a spacer lock comprises fixation features such a notches for use by an attached insertion instrument to provide torsional control over a bone spacer.

In one form, a spacer lock comprises fixation features such a notches for use by an attached insertion instrument to provide counter-torsion forces during torsional insertion of a helical lock.

In one form, a lock guide is in the form of opposing wings extending from a lock aperture but may assume a variety of other non-circular forms that can provide rotational control including for example a hex and a torx shape.

In one form, a spacer includes one or more graft apertures defined by a graft surface on an inner spacer wall.

In one form, bone graft or other bone substitutes may be packed within a graft aperture to encourage fusion between bone portions situated at opposing sides of a spacer.

In one form, a leading end of a spacer is tapered for eased insertion into an intervertebral space.

In one form, an instrument having opposing paddles may be used to wedge open an intervertebral space, then using an inserter tool a spacer is slid into the intervertebral space.

In one form, a helix lock is used to fix a bone spacer in a predetermined position between two bone portions.

In one form, a helix lock is in the form of an open helix.

In one form, a helix lock is absent a shank portion that in a traditional screw would span from one coil or thread to the next coil or thread.

In one form, a helix lock secures bone portions against one or more of an upper spacer surface and a lower spacer surfaces.

In one form, a helix lock comprises several revolutions of a single coiled elongate wire.

In one form, a helix lock comprises several revolutions of two individual coiled elongate wires extending from a proximal end of the helix lock.

In one form, a coiled elongate wire used to form a helix lock may comprise a variety of cross-sectional profiles including circular, 'X', 'Y', 'I', boxed, oblong, elliptical, and triangular shaped.

In one form, a helical lock comprises a generally open central core space along a central axis defined by redundant helical coils of the helical lock.

In one form, a helical lock comprises an open core space wherein said core space is generally cylindrical.

In one form, said core space houses a shaft of a spacer inserter instrument.

In one form, a helical lock slides along a shaft of a spacer inserter instrument positioned within said core space.

In one form, a helical lock cross sectional shape and size is modified to meet predetermined performance requirements.

In one form, a helical lock cutting tip comprises a reduced surface to ease entry into a bone.

In one form, a multi-edge cutting tip is utilizing comprising a series of alternating flutes and cutting edges to provide easier passage into bone.

In one form, a helical lock cutting tip comprises a tip wherein a coil wire is tapered before coming to a sharp mid-line point.

In one form, a helical lock tip is biased towards an outer diameter perimeter of the helix lock coil to improve engagement with the bone.

In one form, a helical lock tip is extends outside the outer diameter perimeter of the helix lock coil to create a cutting path within the bone that biases the bone toward the spacer.

In one form, a cross-sectional profile of a helical lock is adjusted for stiffness in various directions.

In one form, an 'I' shaped helical lock cross-sectional profile has a base of the 'I' positioned adjacent a central helical lock axis and the top of the 'I' is positioned distal a central axis. Strength and stiffness attributes such as these may be used to provide a robust combination of radial stiffness (due to moment of inertia) of a helical lock for cutting through bone while minimizing insertion resistance due to a small cross-sectional profile area of a coil.

In one form, a trailing end of a helical lock comprises a back-out.

In one form, a back-out is in the form of a back-out ear.

In one form, a back-out ear is in the form of lobe or recess positioned for interference with a complementing tooth on a tool for removal of a helix lock by rotation of the lock in an opposite direction.

In one form, a backout ear is adjacent to a butt of the helix lock coil.

In one form, a butt surface on the butt of the helix lock may be used by instrumentation to drive the helical lock into bone.

In one form, a helical lock is fully seated with a spacer and a cutting tip of the helical lock is seated in a tip pocket thereby offering support to the adjacent segment of coil.

In one form, a tip pocket shields the tip from causing unintended damage to nearby tissues and serves as a stop to limit further advancement of the coil such that the helical lock is situated in a predetermined position.

In one form, coils of a helical lock extend through the bone fixing a first vertebrae (V1), a spacer, and a second vertebrae (V2) together as a bundled unit.

In one form, a cutting tip of a helical lock cuts a path between an entry point in an outer wall of a bone then continues to cut through the body of the bone and eventually creates an exit through an outer wall of the bone thereby securing the bone to the bone spacer as the helical lock is threaded therethrough.

In one form, a helical lock prevents endplates of V1 and the endplates of V2 from one or more of lifting and tilting away from an upper and lower surface of a spacer thereby greatly improving the likelihood of a successful fusion.

In one form, a helical lock has a zero-profile when fully inserted within the spacer meaning the implant resides entirely within the intervertebral space.

In one form, no part of a vertebral spacer and helical lock assembly extends beyond an outer wall of vertebrae V1 and V2.

In one form, an operative implant (bone spacer with fully advanced helical lock) comprises an anti-backout feature to prevent undesired backout of a helical lock from its assembled position.

In one form, an anti-backout feature may assume a variety of forms including but not limited to a spring pin seated in a first helical guide that extends into the helical guide once the butt of the helical lock advances past.

In one form, an anti-backout feature in the form of a spring pin is depressed for removal of the helical lock.

In one form, an anti-backout feature in the form of a spring pin is depressed by a removal instrument as an incident of attaching the instrument to the bone spacer.

In one form, an anti-backout feature is in the form of a small screw, a post, a sliding tab, or other structure that will interfere with the backout of the helical lock.

In one form, a helical lock extends only between a spacer and one bone portion.

In one form, two helical locks are used to fixate a bone spacer to two separate bone portions whereby a first helical lock fixates a spacer to a first bone portion and a second helical lock fixes the spacer to a second bone portion. For example, an upper helical lock is used to fix a spacer to V1, and a lower helical lock fixes the spacer to V2.

In one form, whereby two helical locks are used with a single bone spacer, the helical locks may be configured to have intermeshing coils.

In one form, whereby two helical locks are used with a single bone spacer, the helical locks may be configured such that the coils do not intermesh.

In one form, whereby two helical locks are used with a single bone spacer, the helical locks may be configured such that the coils touch but do not intermesh.

In one form, a bone spacer and helical lock instrumentation assembly comprises a spacer inserter portion, a locking rod portion, and a coil driver portion in addition to a bone spacer and one or more helical locks.

In one form, instruments and implants of various sizes in the helical lock instrumentation assembly may be provided to the surgeon in one or more surgical kits such as an individual or combined implant and instrument case.

In one form a spacer inserter comprises a shaft portion extending between an engagement face toward a coupler at a proximal end of the instrument.

In one form, an engagement face of a spacer inserter is configured for abutment against a trailing face of a spacer.

In one form, a spacer inserter engagement face extends one or more of above and below the spacer height so as to also serve as a stop against a bone surface to provide tactile feedback to the surgeon regarding positioning.

In one form, a portion of an engagement face is recessed back proximally to allow further distal insertion of the spacer into a disc space.

In one form, disposed on an engagement face is one or more positioners.

In one form, a positioner is in the form of one or more extended bosses sized and shaped to be received in a lock guide of a spacer.

In some forms, a positioner may assume a variety of forms that serve the function to prevent rotation between an inserter and a spacer.

In one form, a positioner serves to align a longitudinal axis of a spacer with a longitudinal axis of a spacer inserter for precise mating between the spacer and helical lock and in some embodiments for alignment between a helical path on an outer shaft surface of the inserter and a first helical guide.

In one form, a positioner may be sized or shaped to prevent mis-alignment between the inserter and spacer. For example, one positioner may be larger and can only be received in a corresponding lock guide of the same size or shape in a spacer.

In one form, an outer shaft surface of a spacer inserter is smooth and is sized to occupy a core space of a helical lock providing consequential alignment between a longitudinal axis of a helical lock and a longitudinal axis of a complementing spacer.

In one form, a helical path disposed on an outer shaft surface of a spacer inserter is smooth and is sized to occupy a core space of a helical lock providing consequential alignment between a longitudinal axis of a helical lock and a longitudinal axis of a complementing spacer.

In one form, a helical lock slides distally down the outer shaft surface as it is advanced into bone.

In one form, a helical path is disposed on an outer shaft surface. The helical path may be in the form of a groove, bumps, or ridges, or other feature capable of aligning the helical lock such that the tip is aligned with the first helical guide of a spacer.

In one form, a profile of a helical path may vary according to the profile of the helical lock. For example, if the helical lock comprises a round profile wire, the helical path may be in the form of a semi-circular shaped groove.

In one form, a helical path extends sufficiently along an outer shaft surface to fully seat the desired helical lock entirely on the shaft portion before attachment of the spacer.

In one form, a path stop at a proximal end of a helical path may be used to retain the helical lock at the distal end of the spacer inserter.

In one form, a spacer inserter comprises an inner shaft surface defining a central aperture generally extending along axis B.

In one form, a spacer inserter central aperture is sized to slidingly house a locking shaft used to lock a spacer to the spacer inserter.

In one form, proximal from a spacer inserter shaft is a spool window for housing a rotatable spool of a locking shaft.

In one form, an advance surface at a base of the spool window serves to counteract locking forces when the spool of a locking shaft is advanced into the spacer for locking.

In one form, a spacer inserter handle is configured for grasping by a user for inserting a spacer and helical lock instrumentation assembly into a disc space.

In one form, a spacer inserter handle is generally round.

In one form, the inserter handle may comprise a laterally placed portion for generating a counter-torque leverage when advancing a coil driver.

In one form, a coupler may be provided at a proximal end of a spacer inserter for the attachment of additional instruments such as a slap hammer.

In one form, a distal end of an outer shaft surface of a spacer inserter may comprise interchangeable outer shaft sizing cylinders to accommodate for varying helical lock sizes.

In one form, each sizing cylinder may comprise a varying outer diameter 'D2', a constant inter-diameter 'D3' (to slide over and removably restrained on a universal spacer inserter), and a varying cylinder wall thickness 'D4'.

In one form, an outer shaft surface of a spacer inserter may include one or more locator rings. In preferred forms the locator rings are in the form of raised annular rings over which the driver cannula of a coil driver rides.

In one form, a coil driver portion is utilized for driving a helical (helix) lock along an outer shaft of a spacer inserter into a bone and spacer.

In one form, a coil driver comprises an elongate sleeve along an axis 'C' with a proximally placed driver handle portion to transmit torque and axially applied forces down the length of the coil driver instrument.

In one form, a driver handle portion of a coil driver comprises one or more wing portions to assist in applying torque.

In one form, said wing portions are in the form of a bar.

In one form, the offset wings may include one or more finger cups for hand placement.

In one form, a sleeve portion of a coil driver comprises an outer driver surface and an inner driver surface defining a driver cannula.

In one form, a driver cannula is sized for sliding engagement with one or more of an outer shaft surface and one or more locator rings of a spacer inserter.

In one form, a distal end of a coil driver comprises features for driving a helical coil upon advancement of the driver handle of a coil driver.

In one form, a driver tooth extends from a distal end of a coil driver so as to meet the butt surface of the helix lock to drive it forward when the driver handle of a coil driver is rotated.

In one form, a locator tooth is utilized adjacent a driver tooth or on an inner driver surface.

In one form, a locator tooth rides in a helical path keeping a driver tooth aligned with respect to the helical path thus preventing the driver tooth from slipping away from the butt surface of a helical lock.

In one form, a coil driver portion may include a tooth ramp. The tooth ramp is a portion sloped with a similar pitch as the helical lock to complement seating against it.

In one form, a retaining sleeve is included to contain a trailing portion of a helix lock.

In one form, the retaining sleeve is retractable or removable.

In one form, a proximal end of the outer driver surface of a spacer inserter may comprise interchangeable outer sleeve sizing cylinders to accommodate for varying helical lock sizes.

In one form, the location of the driver tooth on the sizing cylinder will vary in distance from Axis C according to the chosen helix lock size.

In one form, a locking rod may be used to secure a spacer to the spacer inserter instrumentation.

In one form, a locking rod comprises an elongated rod portion with an end located distally configured for engagement with a lock aperture of a spacer lock of a spacer.

In one form, the engagement is a threaded engagement between an end of a locking rod and a lock aperture of a spacer lock.

In one form, at a proximal end of a locking rod is a finger spool used to rotate the locking rod to engage rod threads in a spacer.

In one form, a finger spool may be removably fixed to the rod for assembly.

In one form, a lock face on a locking rod abuts against an advance surface on a spacer inserter (or washer therebetween) causing a spacer to be drawn tight to the spacer inserter when the spool is advanced.

In one form, a method for using instrumentation to implant a bone spacer with helical lock comprises the step of positioning a patient on a surgical table according to common access approaches to the surgical space.

In one form, a method for using instrumentation to implant a bone spacer with helical lock comprises the step of monitoring by EMG to locate and avoid nearby nerves.

In one form, a method for using instrumentation to implant a bone spacer with helical lock comprises the step of making incisions at the surgical site along a surgical axis terminating at a space between two bone portions.

In one form, a method for using instrumentation to implant a bone spacer with helical lock comprises the step of using tissue dilators or retractors as necessary to access the surgical site.

In one form, a method for using instrumentation to implant a bone spacer with helical lock comprises the step of using disc preparation instruments to prepare the space between bone portions creating a intervertebral void for the spacer to fit in. In the spine for example, instruments are used to remove disc material in the intervertebral space and roughen the vertebral endplates to enhance fusion.

In one form, a method for using instrumentation to implant a bone spacer with helical lock comprises the step of using sizing instruments to assess the prepared disc space to assist in choosing an appropriate spacer and helical lock implant combination.

In one form, a method for using instrumentation to implant a bone spacer with helical lock comprises the step of supplying instruments and implants in one or more kits to simplify the surgery.

In one form, a method for using instrumentation to implant a bone spacer with helical lock comprises the step of choosing an appropriate sized spacer and corresponding helical lock from a surgical kit.

In one form, a method for using instrumentation to implant a bone spacer with helical lock comprises the step of pre-assembling a locking rod within a central aperture of a spacer inserter.

In one form, a method for using instrumentation to implant a bone spacer with helical lock comprises the step of pre-assembling a coil driver on a shaft of a spacer inserter by sliding the coil driver proximally over the shaft of the spacer inserter.

In one form, a method for using instrumentation to implant a bone spacer with helical lock comprises the step of engaging a locator tooth (if present) of the coil driver within a helical path of the spacer inserter.

In one form, a method for using instrumentation to implant a bone spacer with helical lock comprises the step of choosing appropriate sizing cylinders (if used) corresponding to the chosen sized spacer and helical lock.

In one form, a method for using instrumentation to implant a bone spacer with helical lock comprises the step of fixing the chosen helical lock and chosen bone spacer on the spacer inserter.

In one form, a method for using instrumentation to implant a bone spacer with helical lock comprises the step of loading a helical lock on a shaft of a spacer inserter following a helical path formed on the distal end of the outer shaft surface until abutting the path stop (if present).

In one form, a method for using instrumentation to implant a bone spacer with helical lock comprises the step of aligning a spacer lock portion of a selected bone spacer and aligning along central longitudinal axis D of the bone spacer with longitudinal axis E of the locking rod.

In one form, a method for using instrumentation to implant a bone spacer with helical lock comprises the step of engaging the appropriate positioner of the spacer inserter with the lock guide on the spacer.

In one form, a method for using instrumentation to implant a bone spacer with helical lock comprises the step of the user advancing a finger spool portion of a locking rod to cause the trailing surface of the spacer to be tightened against the engagement face of the spacer inserter as the lock rod engages the lock aperture thereby fixing the spacer to the inserter.

In one form, a method for using instrumentation to implant a bone spacer with helical lock comprises the step of packing a graft aperture in a bone spacer with bone graft or bone substitute.

In one form, a method for using instrumentation to implant a bone spacer with helical lock comprises the step of grasping a spacer inserter handle and moving distally through an incision and tissue into a prepared intervertebral space.

In one form, a method for using instrumentation to implant a bone spacer with helical lock comprises the step of using a tapered nose on the spacer to wedge apart the endplates of adjacent vertebral bodies.

In one form, a method for using instrumentation to implant a bone spacer with helical lock comprises the step of using retractor paddles to wedge apart vertebral bodies of an intervertebral space.

In one form, a method for using instrumentation to implant a bone spacer with helical lock comprises the step of using an engagement face of a spacer inserter to gauge and limit depth of the spacer into an intervertebral space as it abuts the vertebral wall then making final adjustments to the position of the bone spacer in the intervertebral space. Imaging may be used as needed for positional guidance.

In one form, a method for using instrumentation to implant a bone spacer with helical lock comprises the step of holding a spacer inserter handle to keep a bone spacer in a predetermined position within an intervertebral space then applying a torsional force to a driver handle of a coil driver causing the coil driver to advance distally as an incidence of applied torsional and distally directed forces.

In one form, a method for using instrumentation to implant a bone spacer with helical lock comprises the step of using a locator tooth within a helical path of a shaft of a spacer inserter to cause a lead end of a helix lock to advance from the helical path into direct alignment with the first helical guide on a bone spacer.

In one form, a method for using instrumentation to implant a bone spacer with helical lock comprises the step of engaging a driver tooth in a coil driver with a butt surface of a helical lock causing the helix lock to rotatably advance wherein a lead end of the helix lock advances into the first helical guide with cutting tip eventually abutting the vertebral endplate and advancing into it.

In one form, a method for using instrumentation to implant a bone spacer with helical lock comprises the step of advancing a coil driver until a helix lock is fully seated within a bone spacer.

In one form, a method for using instrumentation to implant a bone spacer with helical lock comprises the step of advancing a coil driver until a tip of a helix lock is seated in a tip pocket of a bone spacer or abuts an upper or lower surface of the spacer.

In one form, a method for using instrumentation to implant a bone spacer with helical lock comprises the step of advancing a helix lock until a butt end of the helix lock is housed within a first helical guide.

In one form, a method for using instrumentation to implant a bone spacer with helical lock comprises the step of advancing a helix lock until indicia on an outer shaft surface of a shaft of a spacer inserter indicates the coil driver is fully advanced down the outer shaft surface.

In one form, a method for using instrumentation to implant a bone spacer with helical lock comprises the step of removing instrumentation by derotating a spool on a locking rod to release it from engagement with the bone spacer.

In one form, a method for using instrumentation to implant a bone spacer with helical lock comprises the step of activating an anti-backout feature such as a blocking pin.

In one form, a method for using instrumentation to implant a bone spacer with helical lock comprises the step of commencing standard incision closure procedures.

In one form, a method for using instrumentation to remove a bone spacer with helical lock comprises replacing a coil driver by a reverse coil driver comprising a driver tooth facing in an opposite direction on the spacer inserter then advancing the reverse coil driver against the helix lock and rotating in a counter direction.

In one form, a method for using instrumentation to remove a bone spacer with helical lock comprises the step of a spacer inserter and reverse coil driver are reattached to the spacer by rotation of the locking rod. A reverse coil driver is advanced toward the spacer until a reversed driver tooth engages a backout ear on a helix lock. A driver handle on the reverse coil driver is rotated backing out the helix lock on to an outer shaft surface of the spacer inserter. Implants and instruments are then removed by use of a proximally directed force by the user on the inserter.

In one form, a method for using instrumentation to remove a bone spacer with helical lock comprises the step of attaching a spacer inserter with mounted coil driver to bone spacer. Advancing the coil driver toward the helix lock until a reverse element extending from a distal end of the coil driver engages a reverse surface on a trailing end of a helix lock. Then advancing the coil driver in reverse to back out the helix lock. Then distracting the instrumentation, helix lock, and bone spacer from the intervertebral space.

BRIEF DESCRIPTION OF THE SEVERAL VIEWS OF THE DRAWINGS

These and other features and advantages of the present invention will become more readily appreciated when considered in connection with the following detailed description and appended drawings, wherein:

FIG. 2A is perspective view of one embodiment of a helical lock;

FIG. 2B is a side view of one embodiment of a helical lock;

FIG. 2C is a perspective end view of one embodiment of a helical lock;

FIG. 2D is a perspective end view of one embodiment of a helical lock illustrating one form of a cutting tip;

FIG. 2E is a perspective end view of one embodiment of a helical lock illustrating another form of a cutting tip;

FIG. 2F is a top perspective view of one embodiment of a helical lock having a non-circular coil cross-section;

FIG. 2I is a perspective end view of one embodiment of a helical lock having a recessed form of back out;

FIG. 2J is a partial close-up perspective view of a backout of the helical lock illustrated in FIG. 2I;

FIG. 2K is a perspective end view of one embodiment of a helical lock having a back out ear lobe;

FIG. 2L is a partial close-up perspective view of the back out ear lobe of FIG. 2K;

DESCRIPTION OF SELECTED EMBODIMENTS OF THE INVENTION

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein.

Disclosed herein by written description and illustration are novel forms of bone spacers, spacer locks, instruments for their insertion and fixation to bone, and methods of use in surgery.

The spacers may assume a variety of forms as needed for the desired surgical approach. The spacer forms illustrated are intended for use in lateral lumbar surgical approaches however the spacer may be adapted for use using an anterior, antero-lateral, posterior, direct lateral, or transforaminal approach to the spine or other areas of the body such as sacral-iliac fusion. The spacer and helical lock may be formed from a wide variety of biocompatible materials not limited to titanium, titanium alloys, PAEK, PEEK, PDLA, PPLA, nitinol, stainless steel, cobalt-chrome, and allografts. The implants may also be coated with various surface coatings known in the art to improve bone growth or osteo-integration.

Figure 1:
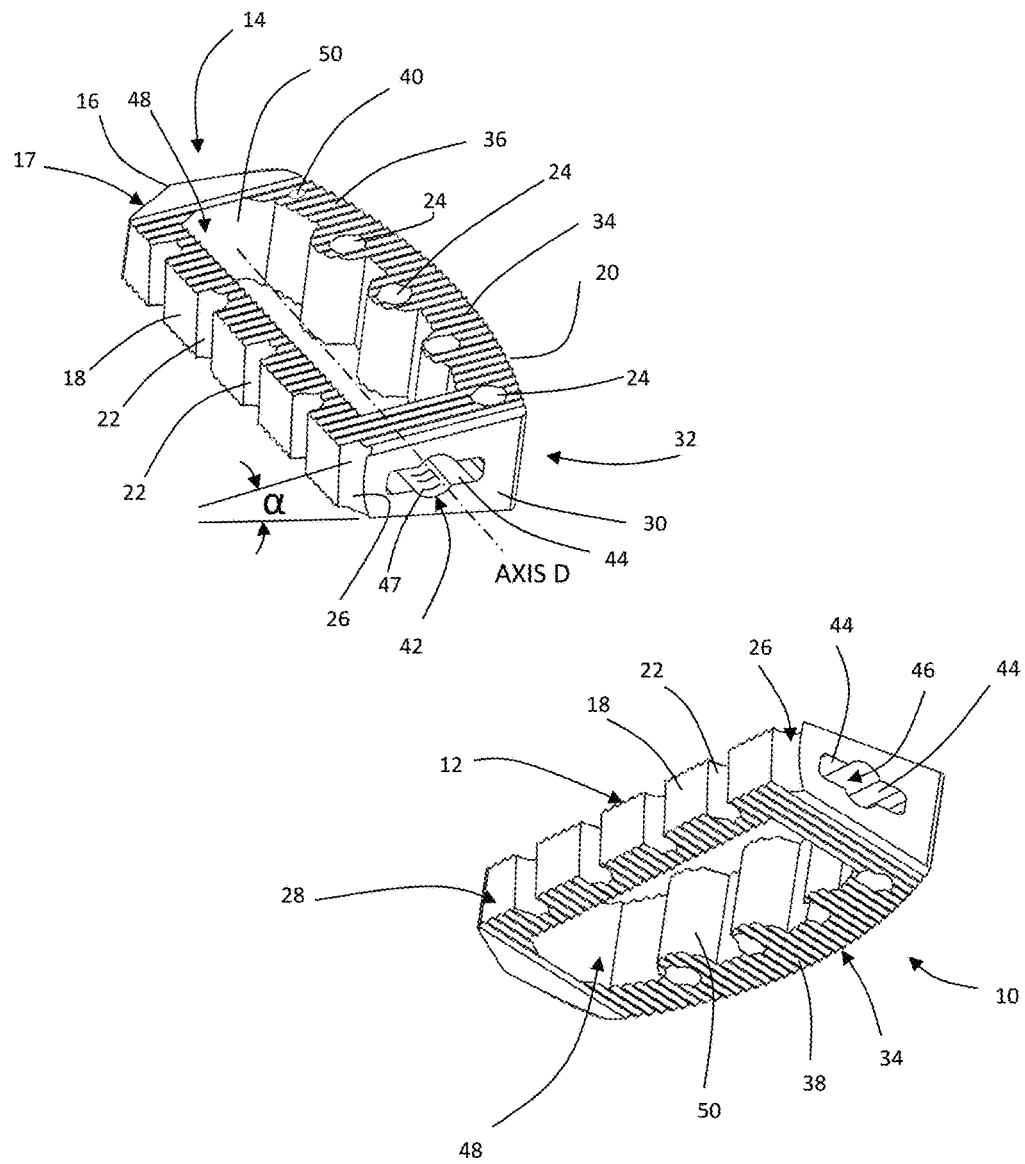
FIG. 1 illustrates a top perspective view (upper figure) and a bottom perspective view (lower figure) of a preferred embodiment of a surgical spacer.

One spacer form suited for a lateral surgical approach is illustrated in two views in FIG. 1. Spacer 10 comprises a spacer body 12 which may include a leading end 14 with a leading surface 16 thereon, a trailing end 32 with a trailing surface 30 thereon, an upper surface 36, a lower surface 38, and teeth disposed on the upper and lower surfaces for the engagement into bone. The upper and lower surfaces 36, 38 may be generally parallel (0 degrees) or be angled up to 12 degrees or more to fit within the space between the bones where the spacer 10 will reside. This angle is illustrated by the symbol a. Upper and lower surfaces 36,38 may be substantially flat or curved (e.g. convex) to match for example the curvature of a spinal endplate.

Formed from spacer body 12 is spacer wall 28 which encircles spacer 10. Spacer body 12 may comprise open helical guides 22 or closed helical guides 24 or both open and closed helical guides to guide a helical lock 54 (FIG. 2A-2L) to predetermined positions and to minimize distortion of a helical lock 54 as it is driven through bone. In some embodiments spacer 10 is manufactured from 3D printing or similar method to accommodate the shape and position of the helical guides which may be difficult or expensive to machine by traditional methods. Body 12 may include a first helical guide 26 used for guiding a distal end 56 and cutting tip 70 of a helical lock 54 thereby making a starter hole at a predetermined location in the bone to assist with proper alignment of the spacer within the bone space. First helical guide 26 may also align a helical path 124 between a spacer inserter instrument 102 and spacer 10 to provide a continuous guide pathway for a helical lock 54 to follow as it is advanced along the instrument 102 into a bone. For example, in some forms a portion of an inserter instrument 102 includes a helical path 124 in which a helical lock 54 is held in preparation for insertion. Helical path 124 on inserter instrument 102 and first helical guide 26 on spacer 10 form a continuous guide for inserting a helical lock 54 at a pre-determined location within the bone.

In some embodiments, spacer 10 includes a tip pocket 40. Tip pocket 40 is a feature for seating a cutting tip 70 of helix lock 54 within body 12 of spacer 10 to provide support for cutting tip 70. Tip pocket 40 may also serve as a stop indicating helix lock 54 is fully engaged as spacer 10 changes from a pre-lock to a fully locked configuration. In preferred forms, tip pocket 40 is in the form of a depression or hole.

A spacer lock 42 on a trailing end 32 of a spacer 10 provides for spacer control by surgical instruments. In preferred forms, the spacer lock 42 comprises a lock aperture 46 which may further comprise lock threads 47 or other fixation features such as notches for use by an attached instrument. One or more lock guides 44 may be used to provide rotational control by an instrument over spacer 10. In the embodiment illustrated in FIG. 1, a lock guide 44 is in the form of opposing wings extending from lock aperture 46 but may assume a variety of other forms that can provide rotational control such as a hex or torx shape.

In preferred forms, the spacer 10 will include one or more graft apertures 48 defined by a graft surface 50 on an inner spacer wall 28. Within graft aperture 48, bone graft or other bone substitutes may be packed therein to encourage fusion between bone portions adjacent upper surface 36 and lower surface 38. In some forms a leading end 14 of a spacer 10 (FIG. 6) may be tapered having a tapered nose 17 for eased insertion into the intervertebral space. In other forms, an instrument having opposing paddles may be used to wedge open the intervertebral space, then using an inserter tool slides the spacer into the intervertebral space.

Figure 2G:
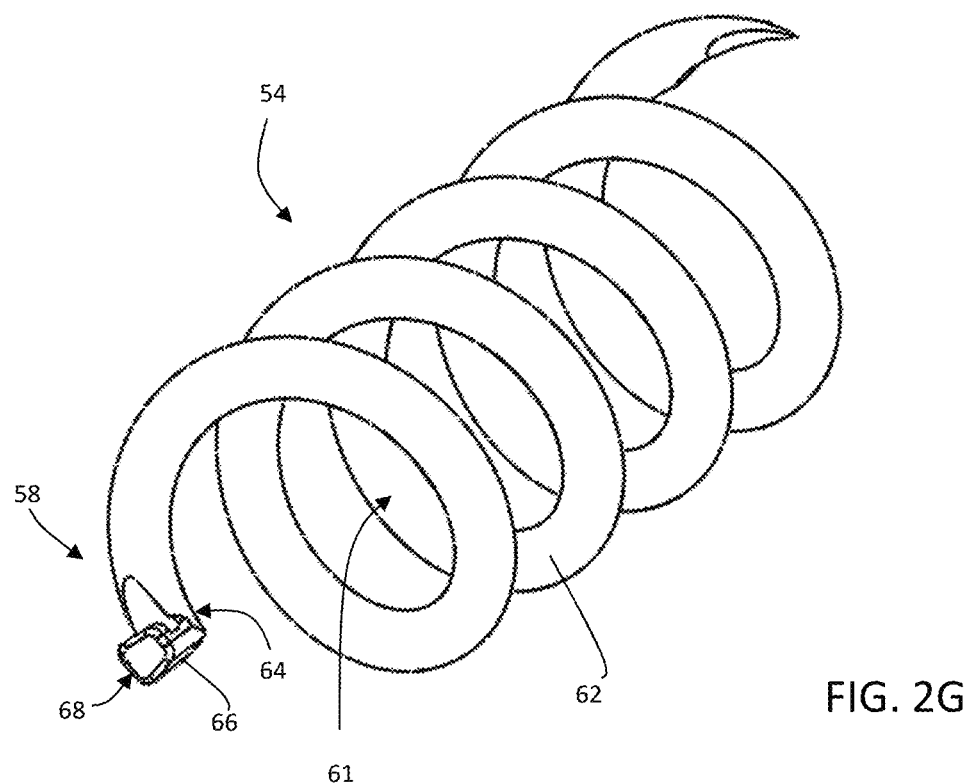
FIG. 2G is a top perspective view of one embodiment of a helical lock having a back out ear lobe.
Figure 2H:
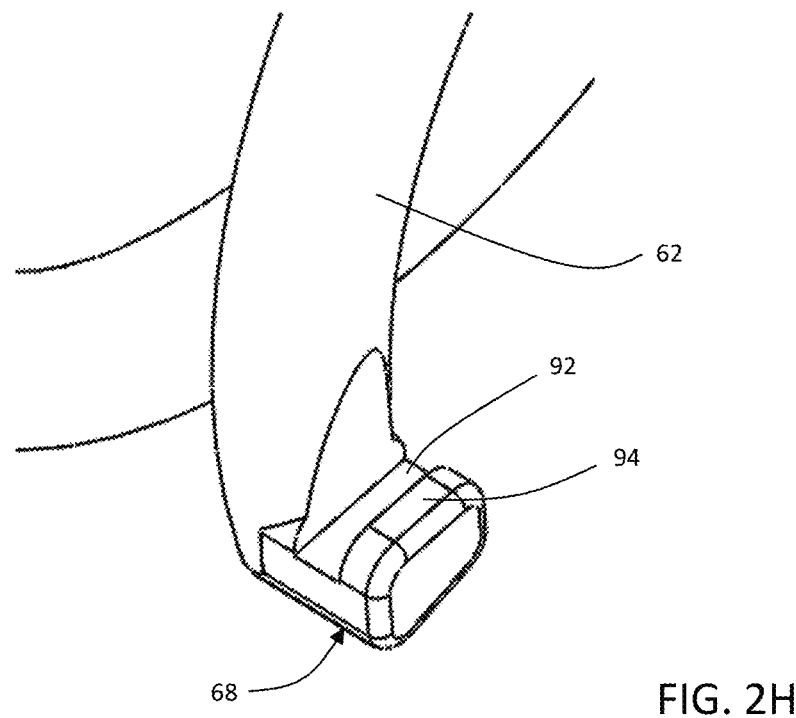
FIG. 2H is a close-up perspective view of a portion of the helical lock illustrated in FIG. 2G.

FIG. 2A illustrates one form of a helix lock 54. In preferred forms a helix lock 54 comprises several revolutions of an elongated wire in the form of a coil 60. An outer surface of the coil is defined by a coil surface 62. The wire may comprise a wide variety of cross-sectional profiles other than the circular profile illustrated. For example, the wire profile may be generally in the form of an 'X', 'Y', 'I', boxed, oval, elliptical or triangular shaped. The wire may be modified to meet predetermined performance requirements. For example, to lower cutting resistance into a bone, a cutting tip 70 having a reduced surface opposing entry into the bone may be used. Varied examples of reduced surface tips are illustrated in FIG. 2A through 2G. In FIG. 2A for example, multiple cutting edges 74 are defined by a plurality of flutes formed within cutting tip 70. In this embodiment, a first flute 76 and a second flute 77 are formed on lateral sides of cutting tip 70. A third flute 79 is formed inward towards a central axis of helix lock 54 as illustrated in FIGS. 2B and 2C. Given this flute arrangement, a point 73 is formed at a coil surface 54 at a maximal distance h from central axis A generally at the outer diameter of coil 60. This maximum point position causes bone to be pulled toward a corresponding upper surface 36 or lower surface 38 of spacer 10 as helix coil 54 is advanced into bone.

FIG. 2D illustrates a plurality of flutes defining a point 73 on coil surface 54 located at a distance h from central axis A that is between an outer coil diameter and an inner coil diameter. FIG. 2E illustrates a plurality of flutes defining a point 73 located at a distance h from central axis A wherein point 73 is generally at an inner coil diameter. In an alternative embodiment, point 73 of coil 60 extends outside an outer diameter perimeter of a helix lock coil. This configuration may be used for example to create a cutting path within the bone that encourages the bone to gravitate toward the spacer more tightly than other configurations.

The profile of a helical lock 54 may be used to adjust for stiffness in various directions. For example, an 'I' shaped helical profile wherein the base of the 'I' is positioned adjacent a central axis A and the top of the 'I' is positioned distal the central axis A, may be used to provide a robust combination of radial stiffness (moment of inertia) of the helical lock for cutting through bone while minimizing insertion resistance due to the small profile area of the wire. As an example of yet another alternative embodiment, FIG. 2F illustrates a helical lock 54 that is wider nearer a central axis A and narrower distal from a central axis A such as this generally triangular shaped profile. A broad inside face 86 of the helical lock 54 limits the ability for helical lock 54 to cut through bone in the event the bone is pulled away from spacer 10. Outside face 88 provides radial stiffness to coil 60. In preferred forms, helical lock 54 comprises a plurality of coils 60. For example, the embodiment illustrated in FIG. 2B comprises approximately four complete revolutions of coils. Multiple coil revolutions provide a broader coil surface 62 to distribute forces to adjacent bone and consequently better fixation with lower incidence of helical lock 54 pullout from the bone. In preferred forms, a helical lock comprises a generally open central core space 61 along a central axis defined by redundant helical coils of the helical lock.

A proximal end 58 of a helical lock 54 may comprise a back out. A back out is a feature on helical lock 54 used for advancing the helical lock 54 in a proximal direction. For example, the backout may be used when removing or repositioning a back out in bone. In some embodiments a back out is in the form a back-out ear lobe 68 extending from a coil surface 62 as illustrated in FIG. 2G, 2H, 2K, 2L. In other embodiments a back out is in the form of a back out recess 90 formed within a coil surface 62 and positioned for interference with a complementing tooth on a tool for removal of a helix lock 54 by rotation of the lock in an opposite direction. A backout ear 68 in preferred forms is adjacent to a butt 64 of a coil 60. A butt surface 66 on the butt 64 of a helix lock 54 may be used by instrumentation to apply torsional forces for driving helical lock 54 into bone. A reverse surface 92 is positioned for application of a torsional driving force in an opposing direction by an instrument. In some embodiments, a back out may comprise a retaining shelf configured to prevent a helical lock 54 removal instrument from unintentionally slipping away from helical lock 54 during application of a back out torsional force.

Figure 3:
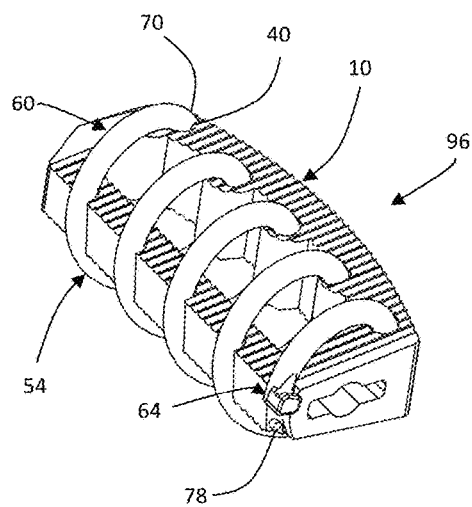
FIG. 3 is a top perspective view of one embodiment of an operative implant comprising a helical lock engaged with a spacer.

FIG. 3 illustrates one embodiment of a helical lock 54 fully seated with a spacer 10. A cutting tip 70 of a helical lock 54 is seated in a tip pocket 40 thereby offering support to the adjacent segment of coil 60. Tip pocket 40 also shields cutting tip 70 from causing unintended damage to nearby tissues and serves as a stop to limit further advancement of a coil such that the helical lock 54 is situated in a predetermined position with respect to spacer 10.

Figure 30:
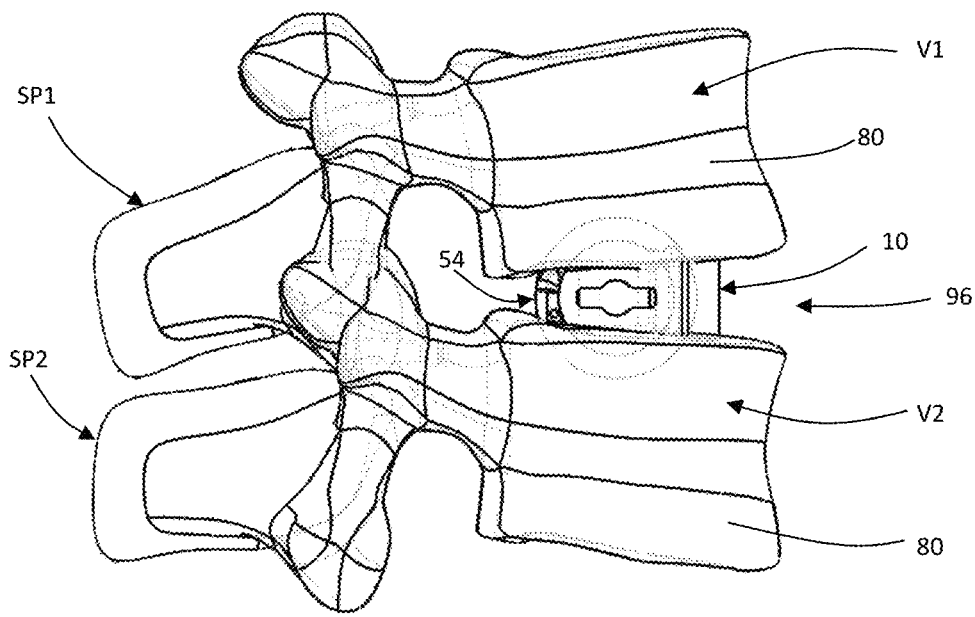
FIG. 30 is a semi-transparent side view illustrating one embodiment of an operative spacer and helical lock implant seated within the intervertebral space and further illustrating helix lock coils engaged within the body of the bone.

FIG. 30 illustrates a side view of a spacer 10 mated with a helical lock 54 in an assembled configuration alternatively referred to as an operative configuration and as an operative implant 96 (spacer with helix lock). In this lateral anatomical view, an operative implant 96 is situated between opposing vertebral body endplates in the spine. In this embodiment the bone portions are labeled V1 for an upper vertebrae and V2 for a lower vertebrae and SP1 for upper spinous process and SP2 for lower spinous process. Coils 60 of helical lock 54 are illustrated extending through the bone fixing V1, spacer 10, and V2 together as a bundled unit. Helical lock 54 prevents vertebral endplates of V1 or V2 from lifting or tilting away from the upper surface 36 or lower surface 38 of spacer 10 thereby greatly improving the likelihood of a successful fusion. In preferred embodiments, helical lock 54 has a zero-profile when fully inserted within a spacer 10 meaning the implant completely resides within an intervertebral space. For example, when utilized as a vertebral spacer, no part of the assembly extends beyond an outer wall of the vertebrae V1 or V2.

Figure 4:
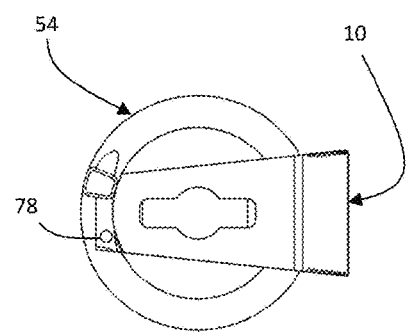
FIG. 4 is an end view of the operative implant illustrated in FIG. 4.

Also, illustrated in FIGS. 3 and 4 is an anti-backout 78 feature. This feature prevents undesired backout of a helical lock 54 from a assembled configuration. The anti-backout feature may assume a variety of forms including but not limited to a spring pin seated in a first helical guide 26 that pops out once a butt 64 of a helical lock 54 advances past. The spring pin is depressed if removal of the helical lock is desired. In some embodiments the spring pin is depressed by the removal instrument as an incident of attaching the instrument to the spacer. In other forms an anti-backout 78 may be a small screw or post or sliding tab or other structure that will interfere with the backout of a helical lock 54.

Figure 5:
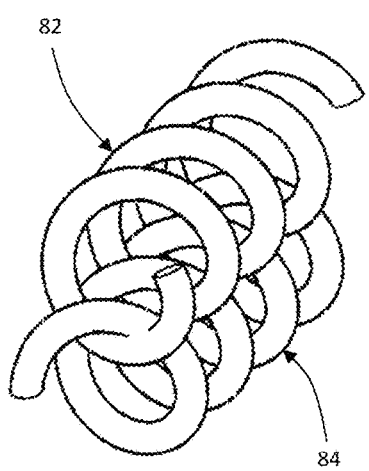
FIG. 5 is a top perspective view of an alternative embodiment of two helical locks intermeshed in an operative configuration with spacer portion removed.
Figure 6:
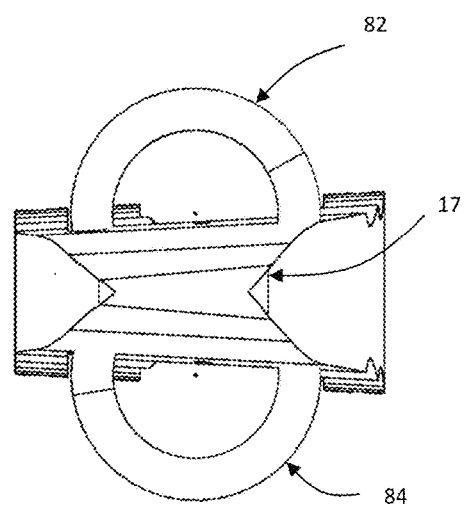
FIG. 6 is an leading end view of the operative implant of FIG. 5 with spacer portion included.

In some forms, a helical lock 54 may extend only between a spacer 10 and one bone portion. For example, as illustrated in FIG. 6, two helical locks may be used. Replacing the spacer-lock assembly in FIG. 4 with a spacer-lock assembly of FIG. 6, an upper helical lock 82 fixes the spacer to V1 (first vertebral body), and a lower helical lock 84 fixes the spacer to V2 (second vertebral body). In some embodiments upper and lower helical locks 82, 84 may be configured to have intermeshing coils as illustrated in FIG. 5. Forces attempting to cause separation between V1 and V2 may be counteracted by the binding of upper helical lock 82 with lower helical lock 84. In other embodiments, the coils do not intermesh. A helical lock securing V1 does not intermesh with a helical lock securing V2. In other embodiments, the individual coils touch but do not intermesh.

Figure 7:
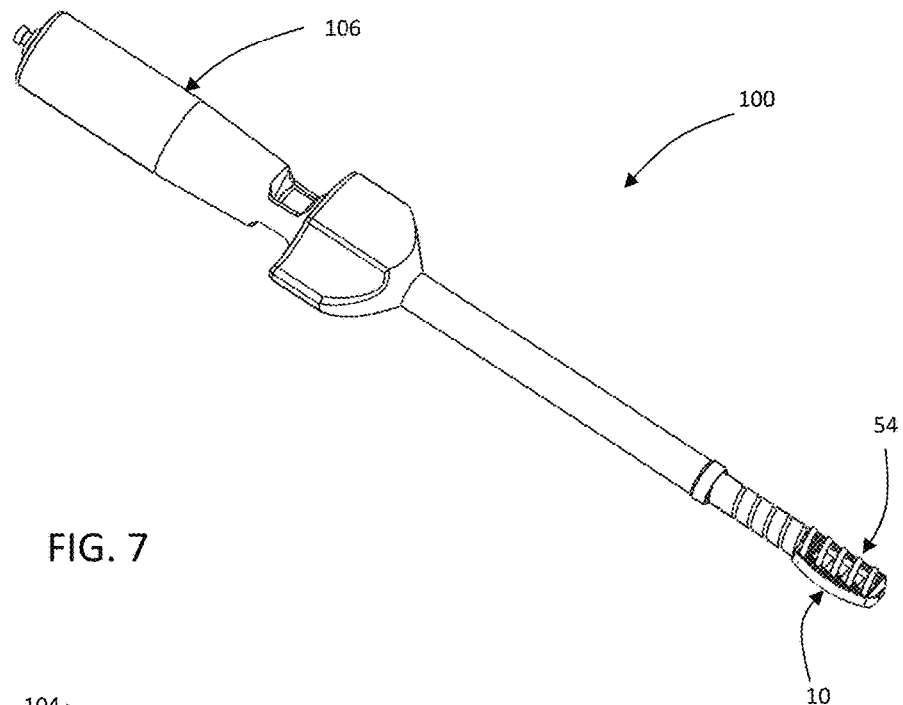
FIG. 7 is a perspective view of a preferred embodiment of a spacer and helical lock instrumentation assembly.
Figure 8:
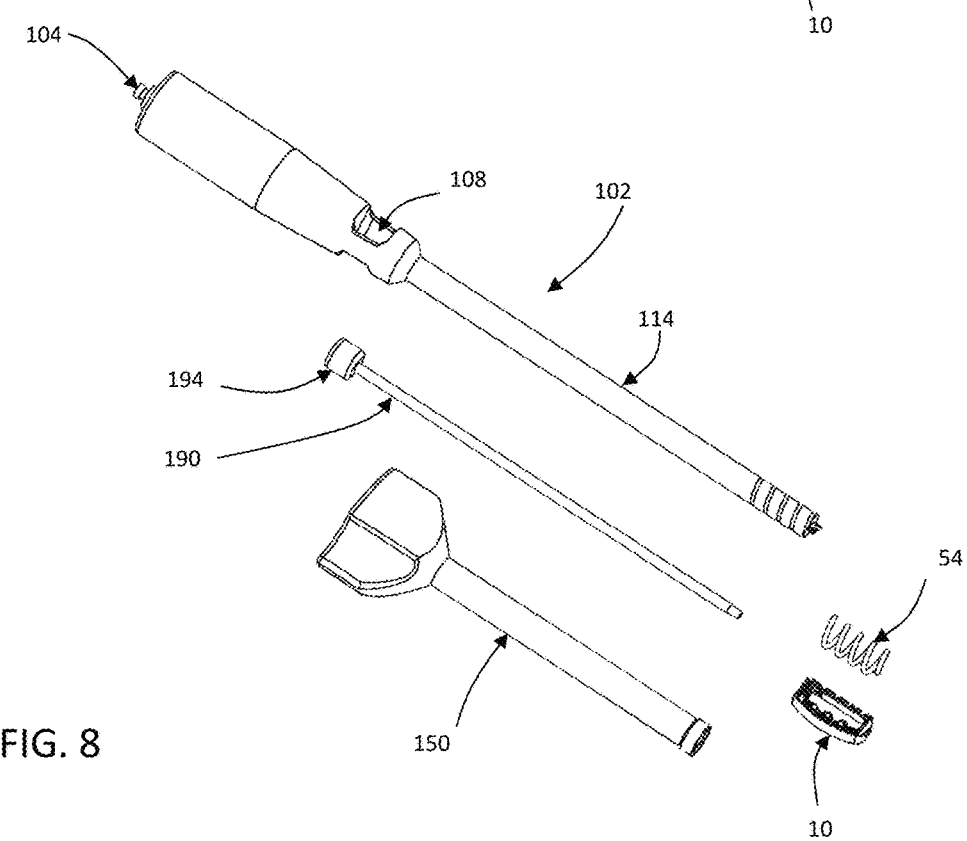
FIG. 8 is an exploded view of the spacer and helical lock instrumentation assembly of FIG. 7.

FIG. 7 illustrates a novel spacer and helical lock instrumentation assembly 100 in an assembled configuration with a spacer and helical lock mounted to the assembly. A spacer and helical lock assembly 100 comprises a spacer inserter portion 102, a locking rod portion 190, and a coil driver portion 150. FIG. 8 illustrates an exploded view of these portions in a preassembled configuration. Instruments and implants of various sizes in the helical lock instrumentation assembly may be provided to the surgeon in one or more surgical kits such as an individual or combined implant and instrument case.

Figure 9:
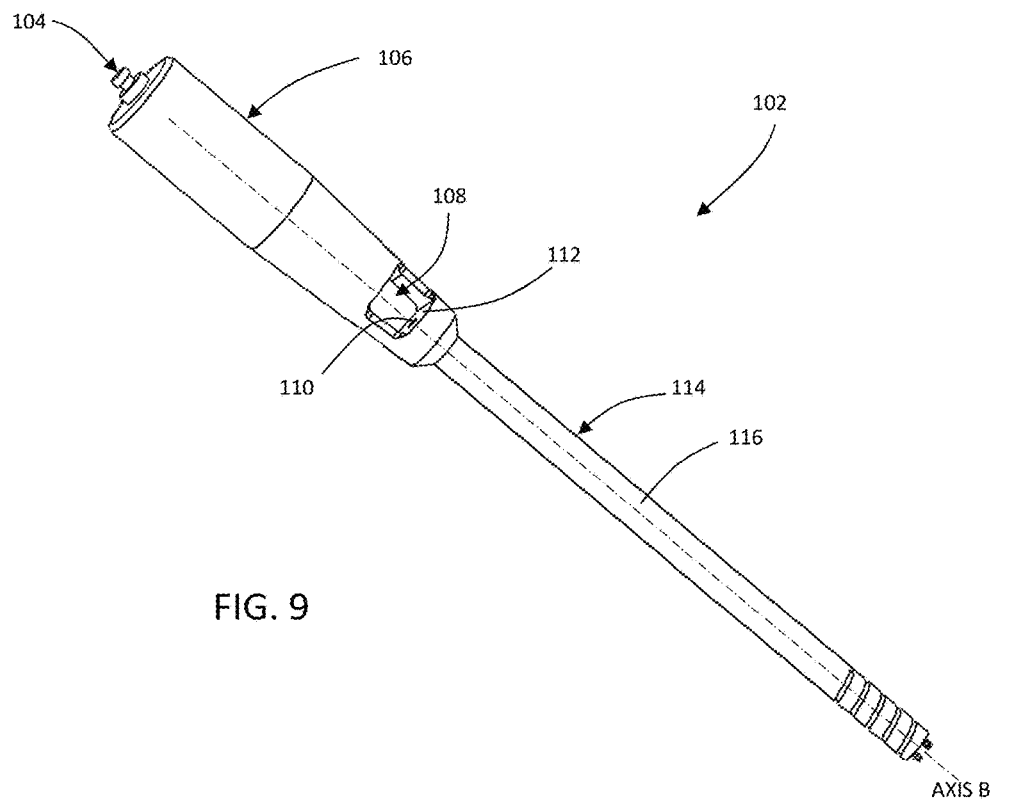
FIG. 9 is a perspective view of one embodiment of a spacer inserter.
Figure 10:
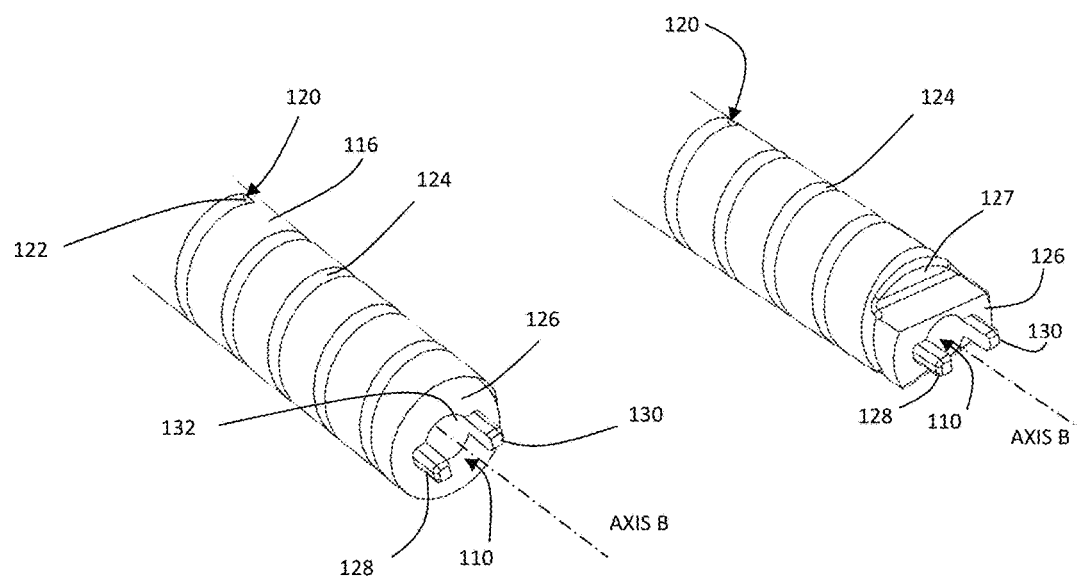
FIG. 10 illustrates two embodiments of distal ends of spacer inserters in partial close-up views. The left view illustrates an engagement face that is uniform therein engaging a spacer and outer wall of a bone along a single plane. The right view illustrates an engagement face and a receded engagement face offset from each other.
Figure 22:
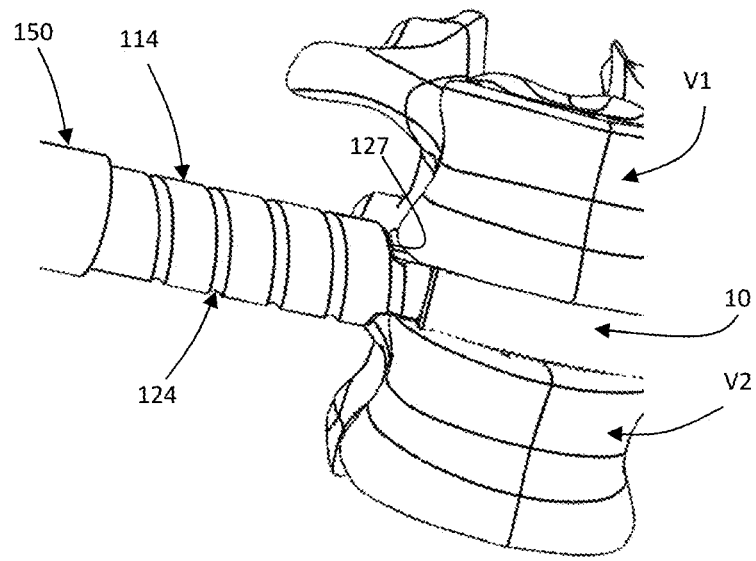
FIG. 22 is a partial perspective view illustrating an alternative step of advancing a helical lock instrumentation assembly through an incision and inserting a spacer into an intervertebral space between two vertebral bodies until a receded engagement face abuts an outer bone wall in a preferred embodiment of a surgical method (helical lock removed)
Figure 23:
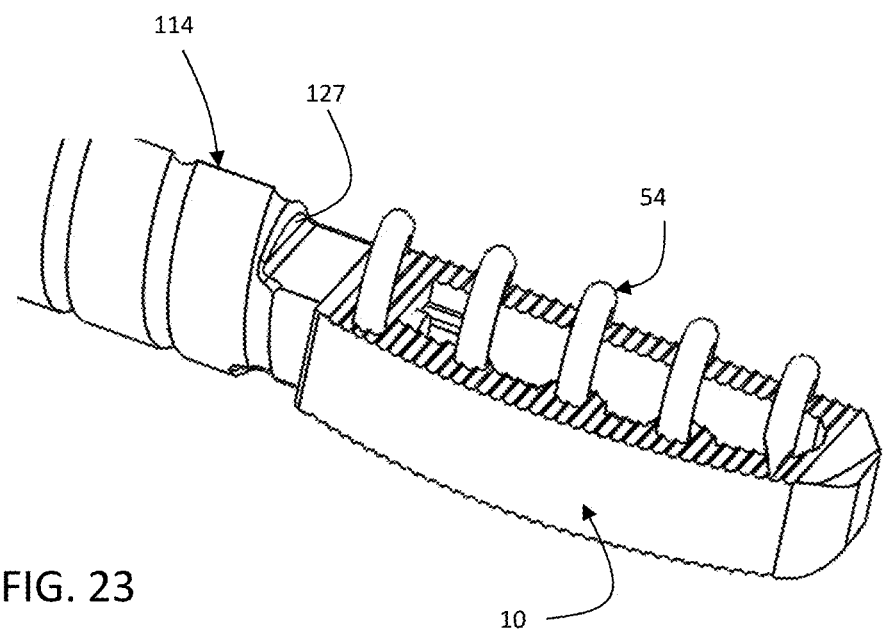
FIG. 23 is a partial perspective view illustrating a helical lock fully seated within a spacer.

FIG. 9 illustrates a preferred embodiment of a spacer inserter portion 102. It comprises a shaft portion 114 extending between an engagement face 126 near a distal end and a coupler 104 at a proximal end of the instrument. Engagement face 126 is configured for abutment against a surface of a spacer 10 such as a trailing surface 30 introduced earlier. In preferred embodiments, engagement face 126 extends above, below, or above and below the corresponding spacer height (distance between upper surface and lower surface of spacer, FIG. 20-21) so as to also serve as a stop against a bone surface to provide tactile feedback to the surgeon regarding positioning. In some embodiments such as illustrated in FIG. 10 (on the right), and FIGS. 22-23, a portion of the engagement face may be recessed back forming a receded engagement face 127 proximally to provide further insertion of a spacer into a bone space such as a disc space. Disposed on engagement face 126 is one or more positioners illustrated here as a first positioner 128 and a second positioner 130 in the form of extended bosses sized and shaped to be received in lock guides 44 of a spacer 10. The positioner may assume a variety of forms that serve the function to prevent rotation between the inserter and spacer. The positioner also serves to correctly align spacer 10 with spacer inserter 102 in the event that alignment between a helical path 124 on an outer shaft surface 116 and first helical guide 26 must be aligned. In some forms a positioner may be sized or shaped to prevent mis-alignment between an inserter 102 and spacer 10. For example, a first positioner 128 or a second positioner 130 may be larger and can only be received in a corresponding lock guide 44 of the same size or shape in a spacer 10.

In some forms, an outer shaft surface 116 is smooth and is sized to occupy and align a helical lock. In this embodiment, a helical lock 54 slides distally down the outer shaft surface 116 as it is advanced into bone. In other forms, a helical path 124 is disposed on an outer shaft surface 116. The helical path 124 may be in the form of one or more grooves, bumps, ridges, and other feature capable of aligning a helical lock 54 such that cutting tip 70 is aligned with a first helical guide 26 of a spacer 10. The profile of a helical path 124 may vary according to the profile of a helical lock. For example, if a helical lock 54 comprises a round profile wire, the corresponding helical path 124 may be in the form of a semi-circular shaped groove. The helical path 124 preferably extends sufficiently along the outer shaft surface 116 to fully seat a desired helical lock 54 entirely on a shaft portion 114 before attachment of a spacer 10. A path stop 120 having a path stop surface 122 may be used to retain a helical lock 54 at a distal end of a spacer inserter 102.

Figure 28:
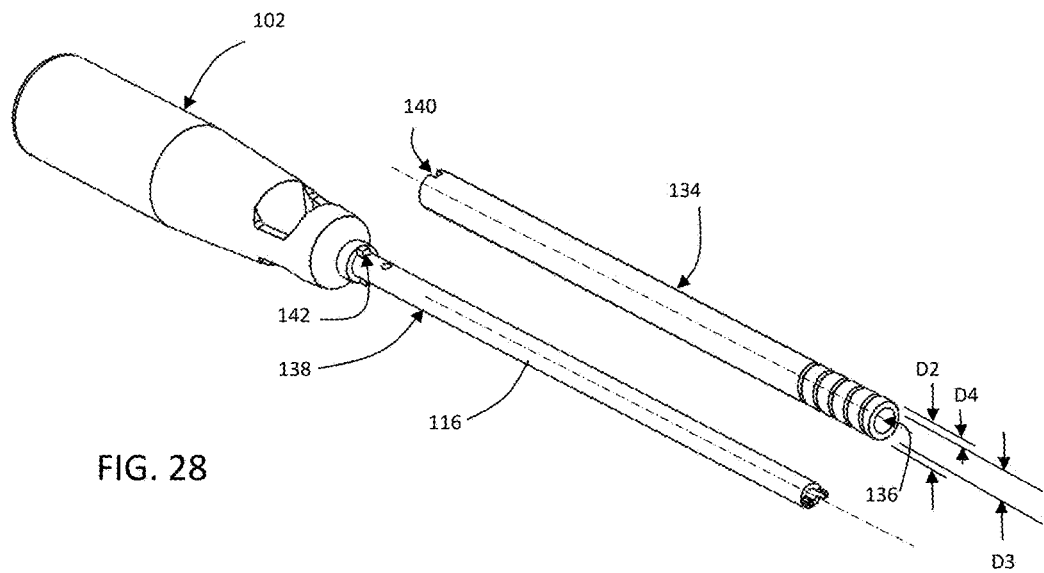
FIG. 28 is an exploded perspective view of an alternative form of spacer inserter comprising interchangeable sizing cylinders to accommodate various sizes of implants.
Figure 29:
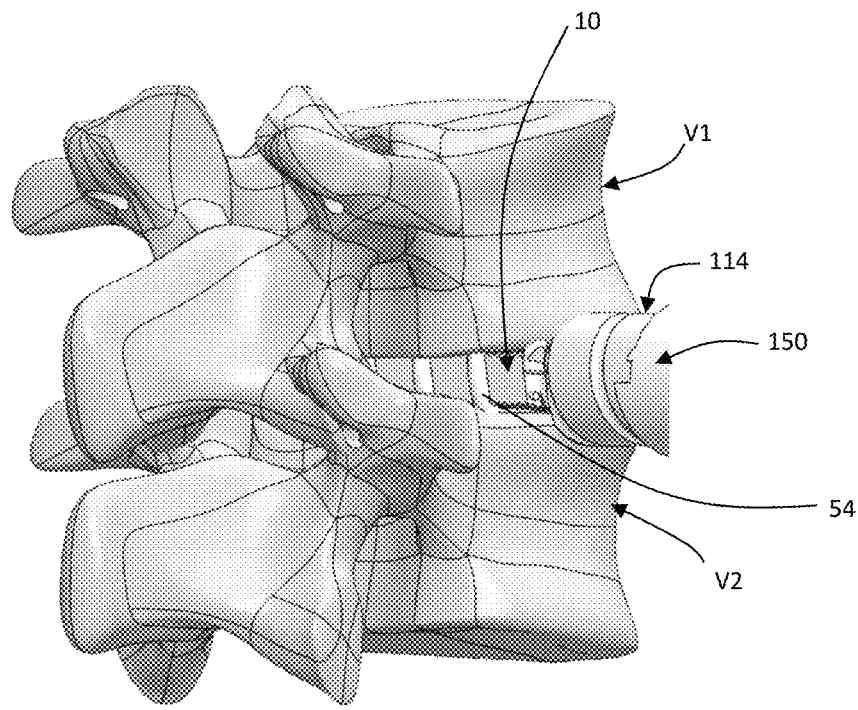
FIG. 29 is a side perspective view of an operative spacer and helical lock implant fully seated within an intervertebral space between two vertebral bodies.

In preferred embodiments a spacer inserter 102 comprises an inner shaft surface 132 defining a central aperture 136 generally extending along axis B (FIG. 10). Central aperture 136 is sized to slidingly house a locking rod 190 such as the one illustrated in FIG. 14. Proximal from shaft portion 114 is a spool window 108 for housing a rotatable spool 194 of a locking rod 190. An advance surface 112 at the base of the spool window 108 is countered by lock face 196 serving to counteract locking forces when spool 194 is advanced causing spacer 10 to be drawn to engagement face 126 for locking. An inserter handle 106 is configured for grasping by a user for inserting a spacer and helical lock instrumentation assembly 100 into a disc space. Inserter handle 106 may be configured in other profiles rather than the round one illustrated. For example, to improve counter torque leverage, the inserter handle may comprise a laterally placed portion for generating torque. A coupler 104 may be provided at a proximal end for the attachment of additional instruments such as a slap hammer. In preferred embodiments, the coupler comprises a mushroom or threaded spool shape. In an alternative embodiment, a distal end of an outer shaft surface 116 comprises interchangeable outer shaft sizing cylinders 134 to accommodate for varying helical lock 54 sizes. In a preferred embodiment (FIG. 28), each outer shaft sizing cylinder 134 may comprise a varying outer diameter 'D2', a constant inter-diameter 'D3' defining sizing central aperture 136 (to slide over and removably restrained on a universal spacer inserter shaft 138), and a varying cylinder wall thickness 'D4'. In some embodiments outer shaft surface 116 may include one or more locator rings. In preferred forms the locator rings 118 are in the form of raised annular rings over which the driver cannula of the coil driver rides.

Figure 11:
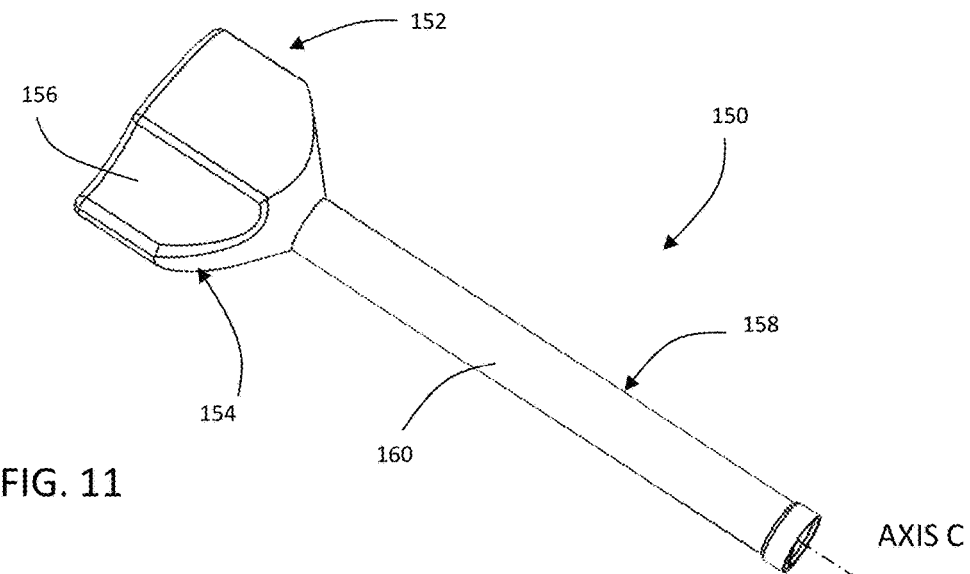
FIG. 11 is a perspective view of one embodiment of a coil driver.
Figure 12:
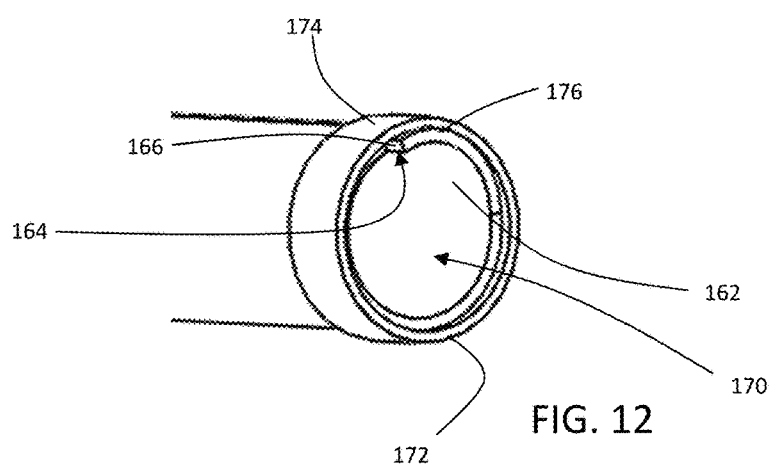
FIG. 12 is a partial close-up perspective view of the distal end of the coil driver illustrated in FIG. 11.
Figure 13:
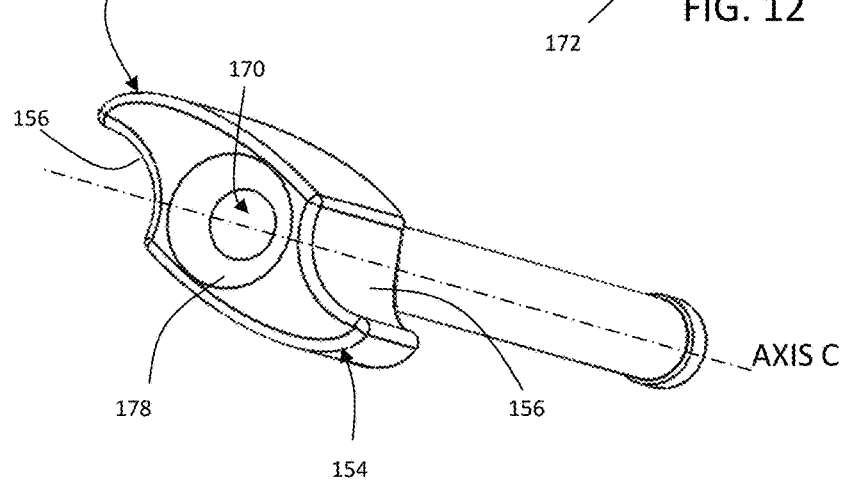
FIG. 13 is a proximal perspective view of one embodiment of a coil driver.

A coil driver portion 150 is utilized for driving a helical (helix) lock 54 along an outer shaft surface 116 of spacer inserter 102 into bone and spacer 10. In one embodiment illustrated in FIG. 11-13, coil driver 150 comprises an elongate sleeve 158 along an axis 'C' with a proximally placed driver handle portion 152 to transmit torque and axially applied forces down the length of the instrument. In preferred embodiments, driver handle portion 152 comprises one or more wing portions 154 to assist in applying torque. The offset wing portions 154 may include one or more finger cups 156 for hand placement. A sleeve portion 158 comprises an outer driver surface 160 and an inner driver surface 162 defining a driver cannula 170. Driver cannula 170 is sized for sliding engagement with outer shaft surface 116 or one or more locator ring of the spacer inserter. The distal end of coil driver 150 comprises features for driving a helical coil upon advancement of driver handle 152. In a preferred embodiment, the first of these features is a driver tooth 164. The driver tooth 164 extends so as to meet butt surface 66 of a helix lock 54 to drive it forward when the driver handle is rotatably advanced. In some embodiments, a locator tooth 168 is utilized extending adjacent the driver tooth 164 or on an inner driver surface 162 toward axis C. The locator tooth 168 is configured in shape and size to ride in the helical path 124 keeping the driver tooth 164 aligned with the path thus preventing driver tooth 164 from slipping away from the butt surface 66 of a helical lock 54. Coil driver portion 150 may include a tooth ramp 176. Tooth ramp 176 is a portion sloped with a pitch generally the same as a cooperating helical lock 54 to complement seating against the helical lock 54. In some forms a retaining sleeve 174 is included on a coil driver to contain a trailing portion of a helix lock 54. In some forms retaining sleeve 174 is retractable or removable. In some embodiments, coil driver portion 150 is provided in a range of sizes corresponding to various diameters of helical coils available to the surgeon and outer shaft 114 sizes of spacer inserter 102. In an alternative embodiment, the proximal end of outer driver surface 160 may comprise interchangeable outer sleeve sizing cylinders to accommodate for varying helical lock sizes. The location of driver tooth 164 on sizing cylinder will vary in distance from Axis C according to the chosen helix lock 54.

Figure 14:
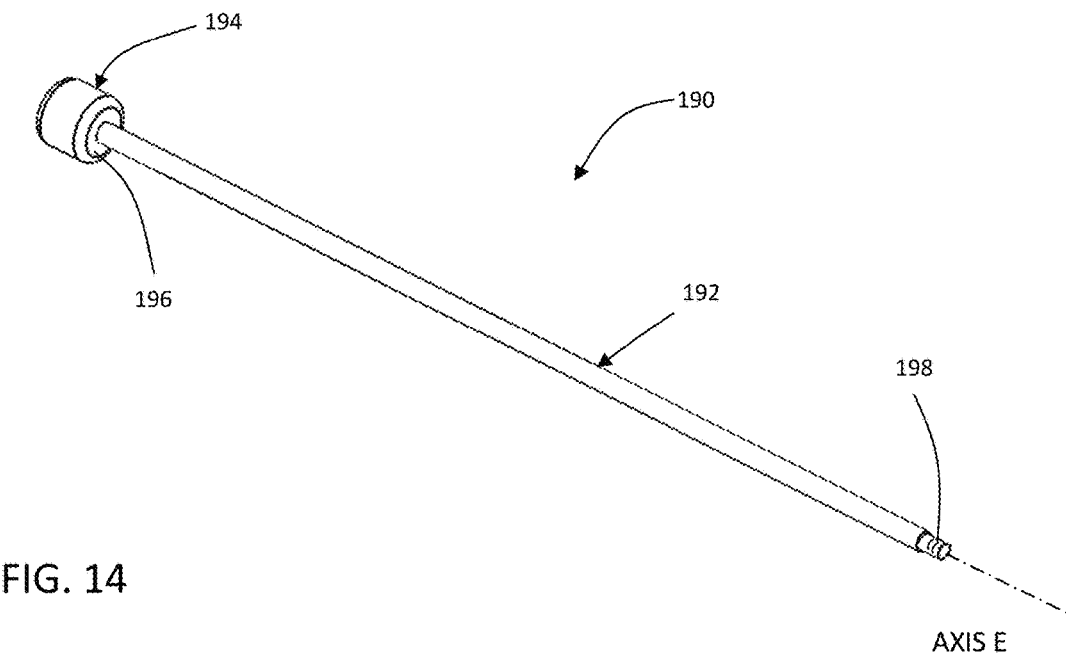
FIG. 14 is a perspective view of one embodiment of a locking rod.

A locking rod 190 may be used to secure spacer 10 to the instrumentation. FIG. 14 illustrates a preferred embodiment of a locking rod 190 comprising a body having an elongated rod portion 192 with a threaded end 198 located distally and configured for threaded engagement with the threaded lock aperture 46 of a spacer lock 42 of a spacer 10. At a proximal end of locking rod 190 is a finger spool 194 used to rotate the locking rod 190 to engage lock threads 47 in spacer lock 42. Finger spool 194 may be removably fixed to elongate rod portion 192 for assembly. A lock face 196 on locking rod 190 abuts against an advance surface 112 on the inserter 102 (or washer therebetween) causing spacer 10 to be drawn tight to spacer inserter 102 when finger spool 194 is advanced.

Figure 15:
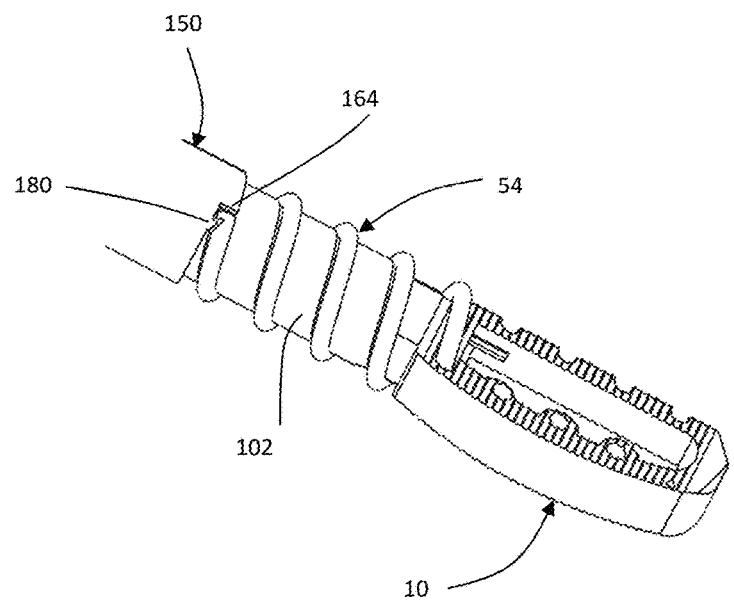
FIG. 15 is a partial close-up perspective view of a spacer and helical lock instrumentation assembly illustrating a coil driver advancing a helix lock into a spacer.

FIG. 15 illustrates a distal end of a spacer and helical lock instrumentation assembly 100. Spacer 10 is secured to spacer inserter 102 and helical lock 54 is residing within helical path 124 of outer shaft surface 116. Locking rod 190 is threaded into the spacer's 10 lock aperture 46. Driver tooth 164 is ready to engage butt surface 66 of helical lock 54 to advance it forward.

In one embodiment, a method for using a helical lock spacer and instruments is illustrated in FIGS. 18-21 and 24-27. The patient is positioned on a surgical table according to common access approaches to the surgical space. Monitoring by EMG may be used to locate and avoid nearby nerves. Incisions to the surgical site are made and tissue dilators or retractors are used as necessary to access the surgical site. Disc preparation instruments are utilized to prepare the space between bone portions creating an intervertebral void for a spacer 10 to fit in. In a human spine for example, instruments are used to remove disc material in the intervertebral space and roughen the vertebral endplates to enhance fusion. Sizing instruments may be used to assess the prepared disc space to assist in choosing an appropriate spacer and helical lock implant combination. Instruments and implants may be provided in one or more kits to simplify the surgery. An appropriate sized spacer 10 and corresponding helical lock 54 is then chosen from the kit.

Figure 18:
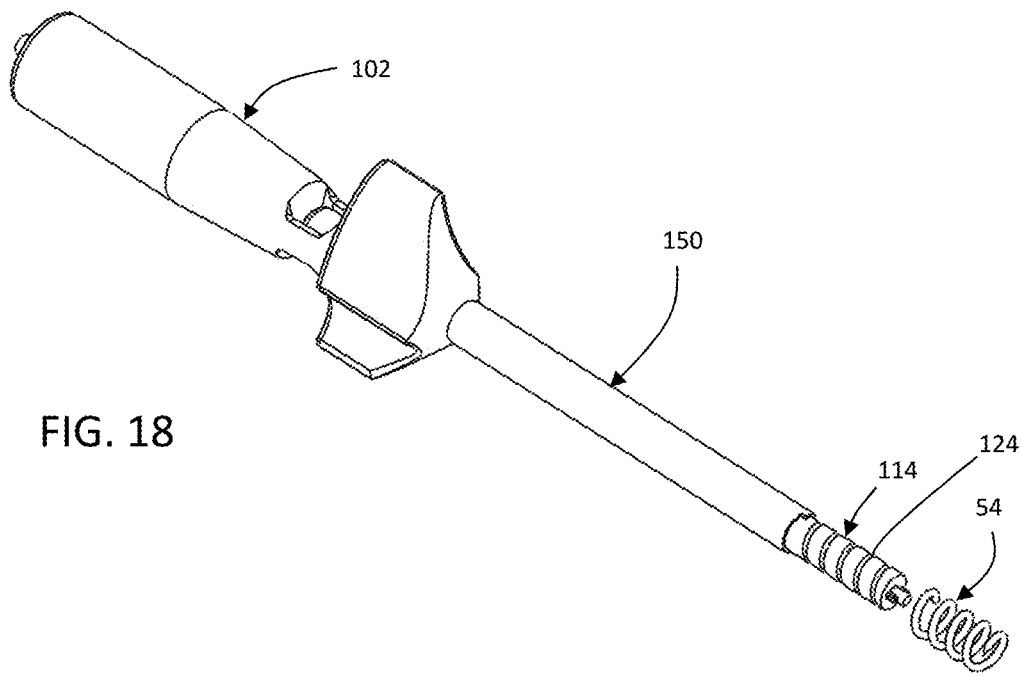
FIG. 18 is a perspective view illustrating a step of preparing to load a helix lock on a shaft portion of a spacer inserter in a preferred embodiment of a surgical method.
Figure 19:
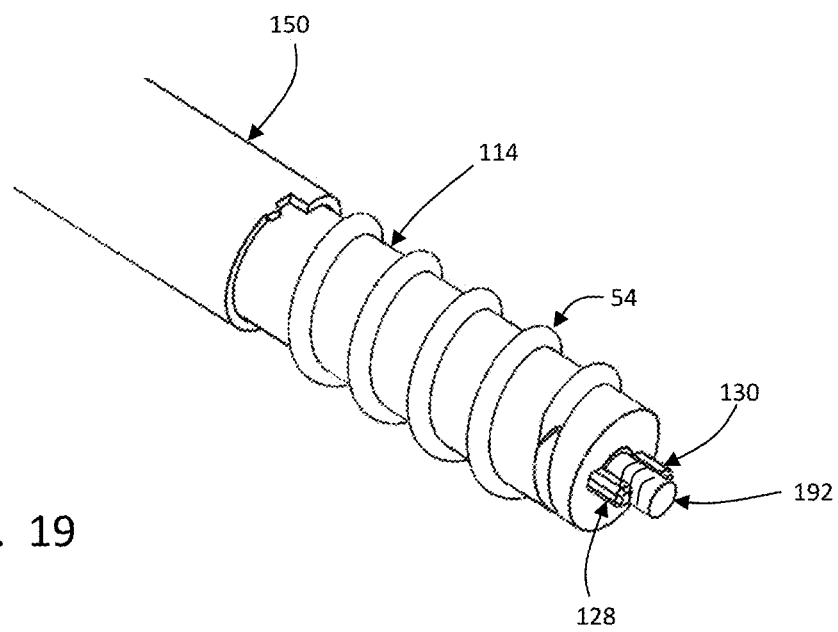
FIG. 19 is a partial close-up perspective view illustrating a step of seating a helix lock on a shaft portion of a spacer inserter in a preferred embodiment of a surgical method.

In preferred embodiments, a locking rod 190 is preassembled within a central aperture 110 of spacer inserter 102. If utilized, the appropriate sizing cylinders 134 corresponding to the sized spacer 10 and helical lock 54 chosen are fixed on the spacer inserter 102 and coil driver 150. Driver cannula 170 of coil driver 150 is slid proximally over shaft portion 114 of spacer inserter 102 as illustrated in FIG. 18. If present, a locator tooth 168 of the coil driver 150 is engaged within a helical path 124 of spacer inserter 102. A chosen helical lock 54 is slid or threaded over a distal outer shaft surface 116 of spacer inserter 102 as illustrated in FIG. 19. If a helical path 124 is present, the helical lock 54 follows the helical path 124 formed on the distal end of the outer shaft surface 116 until abutting the path stop 120 if the path stop is present.

Figure 20:
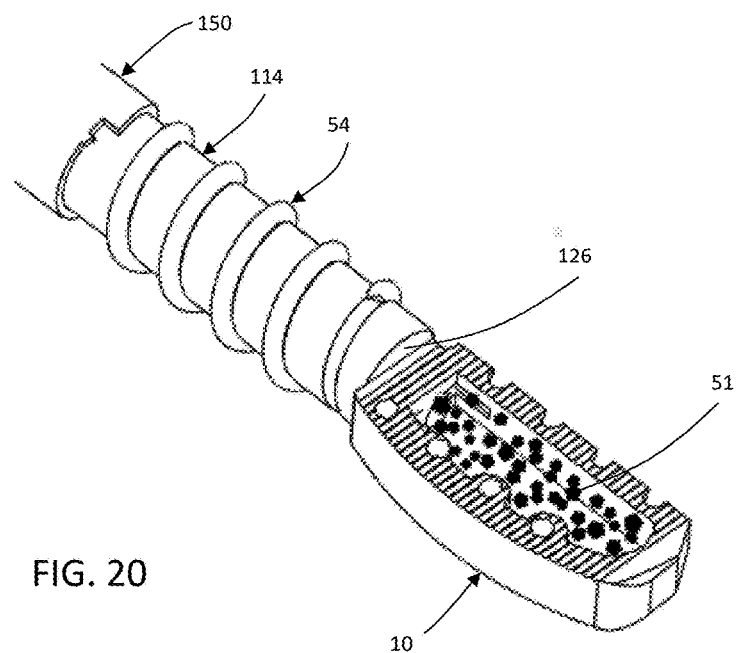
FIG. 20 is a partial close-up perspective view illustrating a step of securing a spacer to a spacer inserter using a locking rod and packing a graft aperture in a spacer with bone graft in a preferred embodiment of a surgical method.

A spacer lock portion 42 of a spacer 10 is then aligned along Axis D with Axis E of the locking rod. The appropriate positioner (i.e. first positioner 128, second positioner 130) of a spacer inserter 102 is engaged with a lock guide 44 on the spacer 10. The user advances the finger spool 194 causing the trailing surface 30 of the spacer 10 to be tightened against an engagement face 126 of a spacer inserter 102 as lock rod 190 engages lock aperture 46. Spacer 10 is now fixed to spacer inserter 102 as illustrated in FIG. 20. The graft aperture may now (or in an earlier step) be packed with bone graft 51 or bone substitute.

Figure 21:
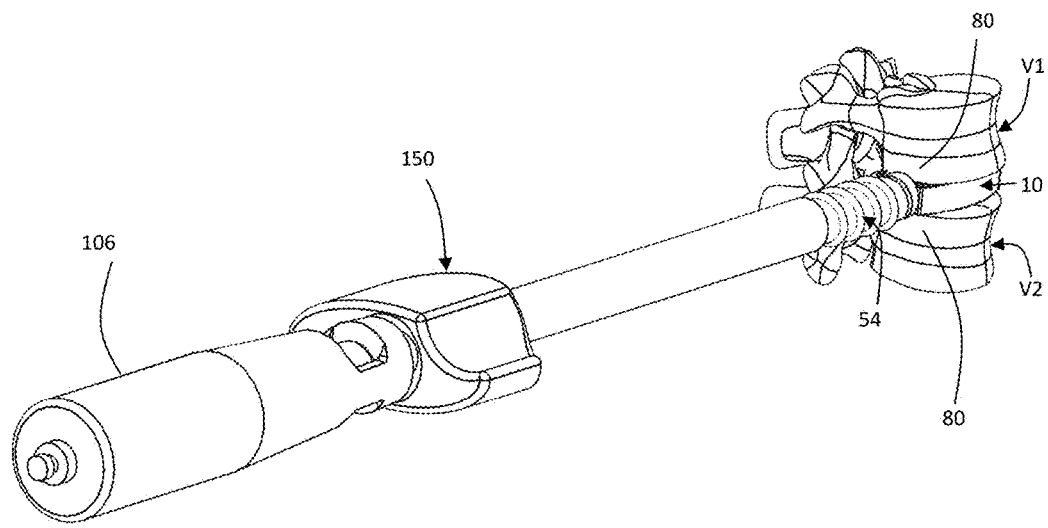
FIG. 21 is a perspective view illustrating a step of advancing a helical lock instrumentation assembly through an incision and inserting a spacer into an intervertebral space between two vertebral bodies until an engagement face abuts an outer bone wall in a preferred embodiment of a surgical method.

Grasping inserter handle 106, the spacer 10 and helical lock instrumentation assembly 100 is moved distally through a prepared incision and tissue into a prepared intervertebral space as illustrated in FIG. 21 (tissue retractors/dilators not shown). If present, a tapered nose 17 on the spacer 10 is used to wedge apart the endplates of the vertebral bodies V1 and V2 otherwise instruments such as retractor paddles may be used. The engagement face 126 of spacer inserter 102 may be used to gauge and limit depth of the spacer 10 into the intervertebral space as it abuts the vertebral wall. Final adjustments are made to the position of the spacer in the intervertebral space. Imaging may be used as needed.

Figure 24:
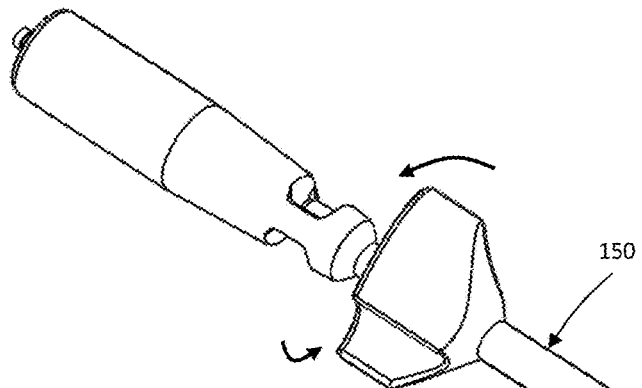
FIG. 24 is a perspective view of a spacer and helical lock instrumentation assembly illustrating a step of a user applying a torsional force to wings of a coil driver handle and advancing a coil driver distally to begin seating a helix lock in bone and within a spacer in a preferred embodiment of a surgical method.
Figure 25:
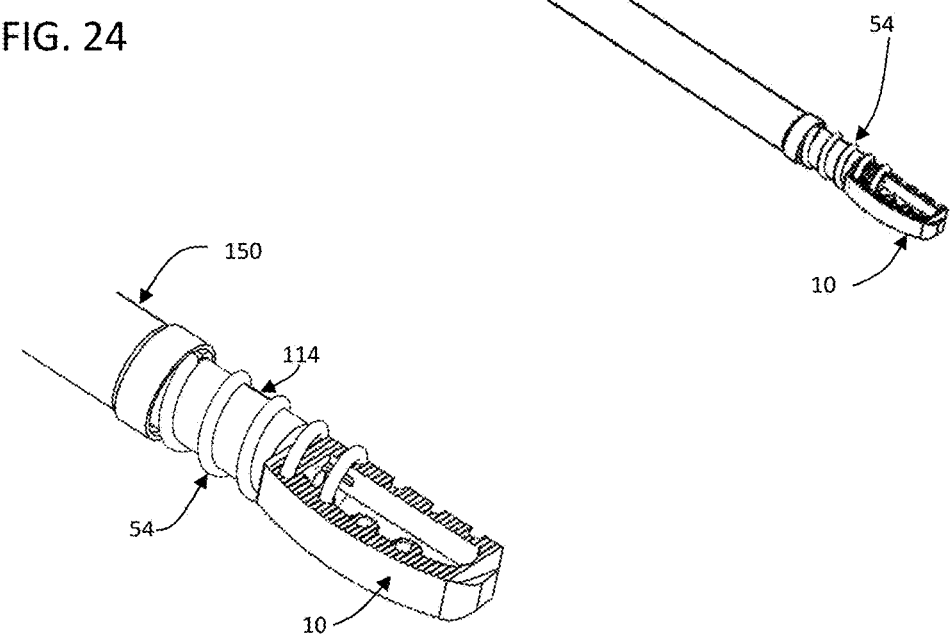
FIG. 25 is a partial close-up perspective view of the step illustrated in FIG. 24.

While holding inserter handle 106 to keep spacer 10 in a predetermined position, the user applies a torsional force to driver handle 152 of coil driver 150. Coil driver 150 will advance distally as an incidence of the applied torsional force; however, a distally directed force on coil driver 150 may be needed in the absence of a locator tooth 168 or thread on a coil driver 150 engaging a helical path 124 on spacer inserter 102. In the presence of a helical path 124 with complementing locator tooth 168, the lead end of a helix lock 54 will advance from the helical path 124 into direct alignment with a first helical guide 26. Driver tooth 164 engages butt surface 66 of helical lock 54 causing helix lock 54 to rotatably advance. The lead end of helix lock 54 advances into first helical guide 26 with cutting tip 70 eventually abutting the vertebral endplate. As incidence of continued torsional advancement of driver handle 152, the lead end of the helix lock 54 advances into the bone and spacer 10 as illustrated in FIGS. 24 and 25.

Figure 26:
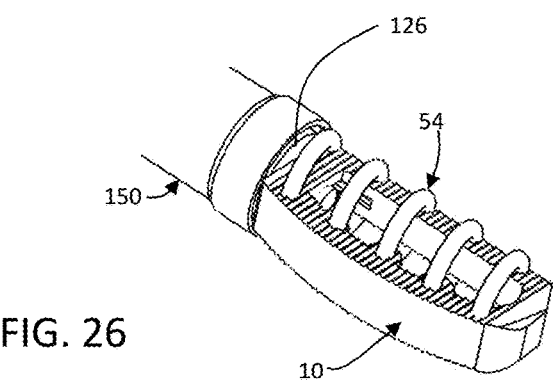
FIG. 26 is a close-up perspective view of a step of fully advancing a helix lock into bone and a spacer in a preferred embodiment of a surgical method.
Figure 27:
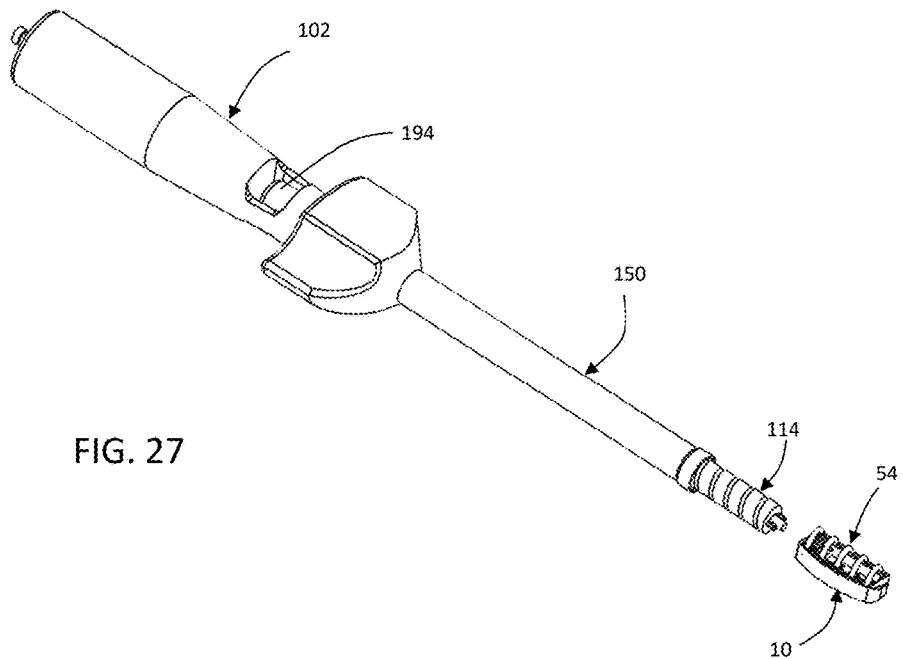
FIG. 27 is a perspective view illustrating the step of reversing a locking rod causing the release of an operative implant from the insertion instruments in a preferred embodiment of a surgical method.
Figure 31:
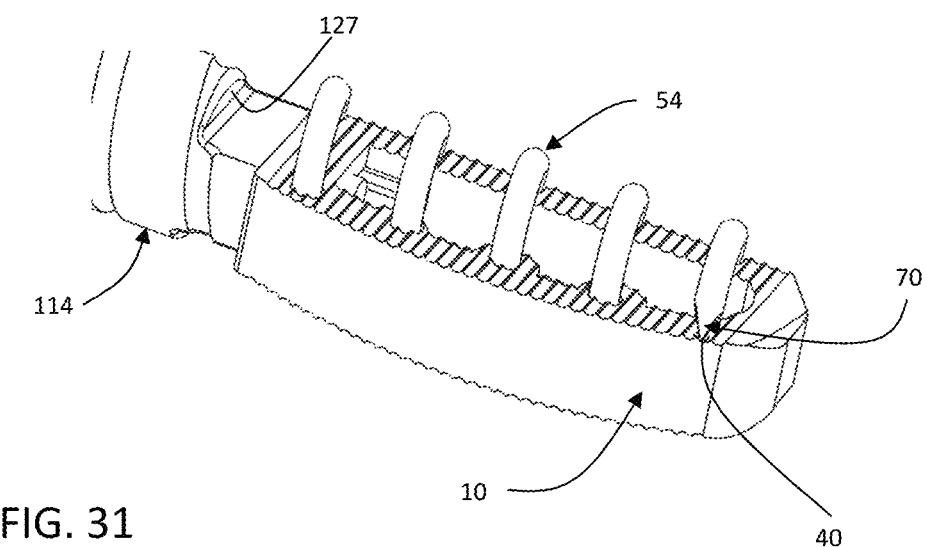
FIG. 31 is a partial perspective view illustrating one embodiment of cutting tip of a helical lock seating within a tip pocket of a spacer.

The coil driver continues to be advanced until the helix lock is fully seated as illustrated in FIG. 26. This occurs when the tip of the helix lock is seated in the tip pocket or abuts the upper or lower surface of the spacer as illustrated in FIG. 31. Alternatively, helix lock 54 is fully seated when butt end 64 of helix lock 54 is housed within first helical guide 26. As yet another alternative, helix lock 54 is fully seated when indicia on outer shaft surface 116 indicates the coil driver 150 is fully advanced down the outer shaft surface 116. As yet another alternative, helix lock 54 is fully seated when point 73 abuts an upper surface 36 or lower surface 38 on the spacer. Operative implant 96 is now in a fully locked and operative configuration. Positioning may be verified by imaging.

The instrumentation is removed (FIG. 27) by de-rotating finger spool 194 on locking rod 190 to release it from engagement with spacer 10. An anti-backout 78 feature such as a blocking pin may now be activated to prevent unintended back out of helical lock 54. Standard incision closure procedure follows.

In the event the helical lock 54 needs to be removed, a reverse coil driver (not shown) having locator tooth removed and comprising a driver tooth facing the opposite direction may be used. Coil driver 150 is replaced by a reverse coil driver on spacer inserter 102. The spacer inserter 102 and reverse coil driver are reattached to the spacer by rotation of the locking rod. The reverse coil driver is advanced toward the spacer 10 until the reversed driver tooth engages the backout ear. The driver handle on the reverse coil driver is rotated causing consequent backing out of the helix lock 54 on to the outer shaft surface 116 of spacer inserter 102. The implants and instruments are then removed by use of a proximally directed force by the user on the inserter.

Figure 16A:
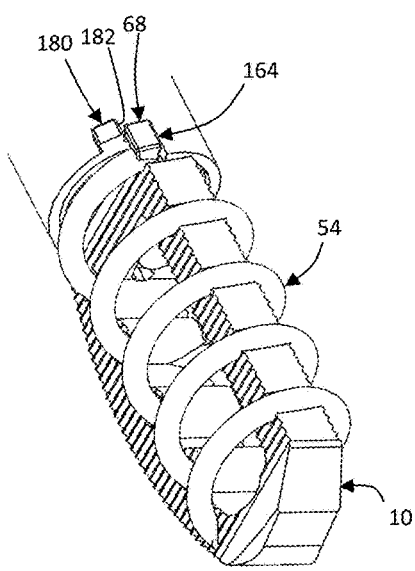
FIG. 16A is a partial close-up perspective view of the interaction between one form of helix lock and a coil driver having back out capabilities.
Figure 16B:
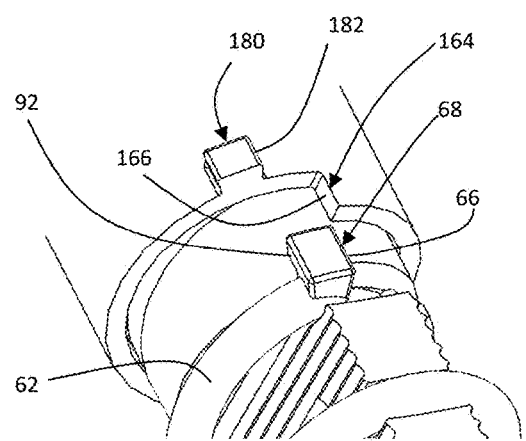
FIG. 16B is a partial close-up perspective view of the interaction between one form of helix lock and a coil driver having back out capabilities.
Figure 17:
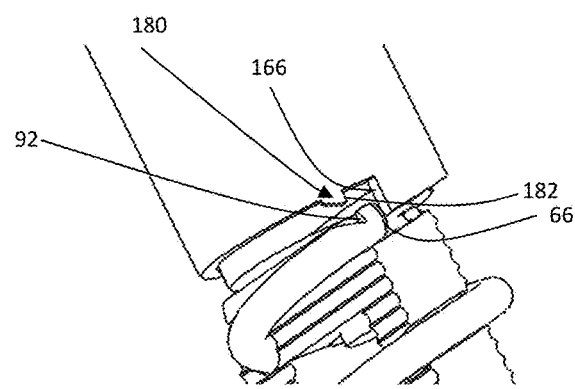
FIG. 17 is a partial close-up perspective view of the interaction between another form of helix lock and a coil driver having back out capabilities.

In alternative embodiments, a back out feature is integrated into a coil driver 150 with complementing features integrated into a helical lock 54. For example, FIG. 2G illustrates one embodiment of a helical coil 54 having an integrated back out ear lobe 68 at a proximal end 58 protruding from coil surface 62. Back out ear lobe 68 comprises a reverse surface 92 generally opposite butt surface 66 for application of back out forces to helical lock 54. Back out ear lobe 68 may also comprise a retaining shelf 94 (FIG. 2H) to contain a reverse element 180 on coil driver 150 from slipping off back out ear lobe 68. In other embodiments, back out ear lobe 68 is absent a retaining shelf 94 as illustrated in FIG. 2L. FIGS. 16A and 16B illustrate one embodiment of the interaction between a back out ear lobe 68 and reverse element 180 integrated into the distal end of coil driver 150. Reverse wall 182 on reverse element 180 imposes reversing torsional forces from a user to reverse surface 92 on back out ear lobe 68 for removal of helical lock 54. Conversely, driver tooth 164 of coil driver 150 imposes advancing torsional forces on butt surface 66 of helical lock 54 when advancing helical lock 54 into bone. FIG. 16A illustrates back out ear lobe 68 situated between driver tooth 164 and reverse wall 182.

In an alternative embodiment (FIG. 15,17), reverse element 180 protrudes directly into a recess 90 formed within coil surface 62 whereby reverse element 180 occupies recess 90 and reversing forces are imparted from reverse wall 182 to reverse surface 92.

Figure 32:
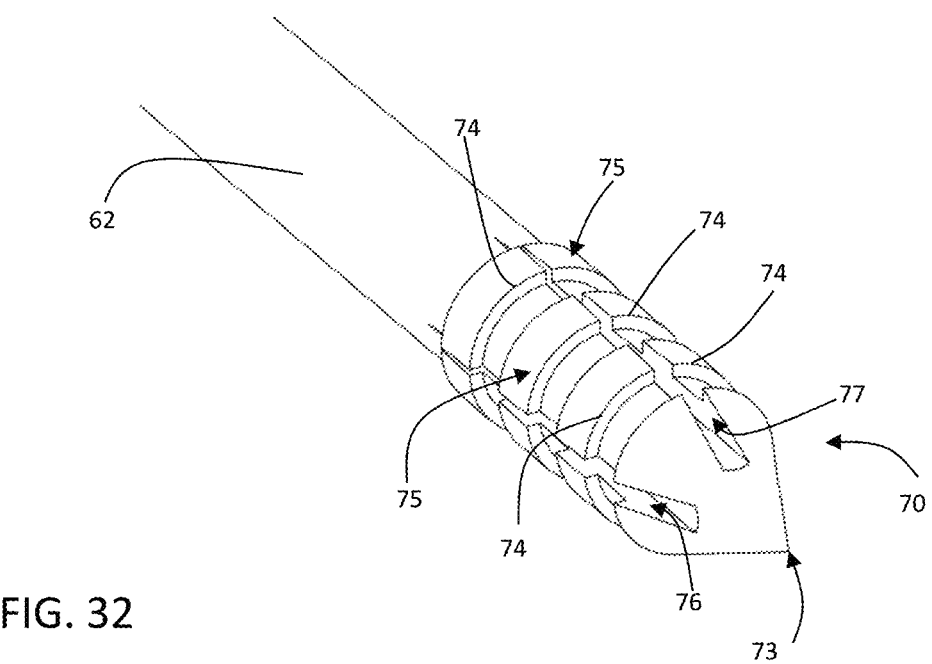
FIG. 32 is a partial perspective view of one embodiment of a cutting tip of a helical lock in a pre-coiled configuration illustrating various flutes and cutting ribs.

FIG. 32 illustrates an alternative cutting tip 70 of a helical lock 54 in a pre-coiled configuration. Cutting tip 70 comprises a plurality of flutes illustrated here as a first flute 76 and a second flute 77 extending from a distal end and moving proximally. Cutting tip 70 may also comprise one or more cutting bands 75 having cutting edges 74 directed distally to assist in cutting bone as the helix lock 54 is torsionally advanced. In some embodiments, the cutting tip may have a diameter that is larger than the diameter of the coils to assure eased insertion after cutting tip 70 lays an initial path.

The foregoing invention has been described in accordance with the relevant legal standards, thus the description is exemplary rather than limiting in nature. Variations and modifications to the disclosed embodiment may become apparent to those skilled in the art and fall within the scope of the invention.

The invention claimed is:

1. A method of implanting a bone spacer having a helical lock in an intervertebral space comprising the steps of:
    obtaining a bone spacer inserter instrument comprising an elongate shaft portion and a central locking rod portion;
    positioning a coil driver over said elongate shaft portion of said bone spacer inserter;
    loading a helical lock implant on a distal end of said elongate shaft portion wherein said elongate shaft portion occupies a central core space of said helical lock and wherein a cutting tip of said helical lock is orientated distally on said bone spacer inserter;
    positioning a bone spacer implant against an engagement face disposed on a distal end of said elongate shaft portion;
    advancing said locking rod portion into a spacer lock of said bone spacer thereby fixing said bone spacer implant to said bone spacer inserter instrument;
    advancing the bone spacer and helical lock instrumentation assembly through an incision and into a predetermined position in an intervertebral space;
    advancing through rotation said coil driver about its central axis thereby driving a tooth face on said coil driver to transmit torsional forces against a butt surface of a helix lock;

and continuing torsional forces on said coil driver until said helix lock is fully threaded into adjacent vertebral bone and said bone spacer.

2. The method of claim 1 further comprising the step of packing a graft aperture of said bone spacer with bone graft or bone graft substitute before advancing into an incision.

3. The method of claim 1 wherein the step of loading a helical lock on a distal end of said elongate shaft portion wherein said elongate shaft occupies a central core space of said helical lock and wherein a cutting tip of said helical lock is orientated distally further comprises the step of seating the coils of said helical lock within a complementary helical path on said elongate shaft portion.

4. The method of claim 1 further comprising the step applying a counter torque to the spacer inserter handle while simultaneously applying a torsional force said coil driver.

5. The method of claim 1 further comprising the step of threading said helical lock through at least one closed helical guide at a leading end of said bone spacer.

6. The method of claim 1 further comprising the step of threading said helical lock through at least one open helical guide at a leading end of said bone spacer.

7. The method of claim 1 further comprising the step of using a first helical guide on said spacer to guide a cutting tip of said helical lock to a vertebral endplate entry site.

8. The method of claim 1 further comprising the step of obtaining said spacer inserter, said coil driver, said locking rod, said bone spacer, and said helical lock from a surgical kit.

9. The method of claim 1 wherein the step of continuing torsional forces on said coil driver until helix lock is fully threaded into adjacent vertebral bone and bone spacer further comprises the step of advancing a cutting tip of said helix lock through a surface of a bone, through the body of the bone, then out a surface of a bone.

10. The method of claim 1 further comprises engaging and transmitting reverse torsional forces through a reverse element on a coil driver to a reverse surface on a helix lock to remove said helix lock.

11. The method of claim 1 wherein the step of positioning a bone spacer against an engagement face disposed on a distal end of said elongate shaft portion of said spacer inserter further comprises the step of engaging one or more positioners on said spacer inserter with one or more lock guides on said bone spacer.

12. The method of claim 1 wherein the step of continuing torsional forces on said coil driver until said helix lock is fully threaded into adjacent vertebral bone and bone spacer further comprises the step of seating a cutting tip of a helix lock into a tip pocket on said bone spacer.

13. The method of claim 1 further comprising the step of activating an anti-backout to prevent unintended back out of said helix lock from the bone spacer.

14. The method of claim 1 further comprising the step of insertion of a second helix lock to secure an adjacent bone to the bone spacer.

15. The method of claim 1 further comprising the step of insertion of a second helix lock in a bone spacer wherein said first helix lock and second helix lock are positioned to have intermeshing coils.

16. The method of claim 1 wherein the step of loading a helical lock on a distal end of said elongate shaft portion wherein said elongate shaft occupies a central core space of said helical lock and wherein a cutting tip of said helical lock is orientated distally on said bone spacer inserter further comprises the step of loading said helical lock until a butt surface of said helical lock abuts a path stop surface on said bone spacer inserter.

17. The method of claim 1 wherein the step of advancing a locking rod into a spacer lock of said bone spacer thereby fixing said bone spacer to said bone spacer inserter further comprises the step of applying a rotating force to a finger spool coupled to said locking rod.

18. The method of claim 1 wherein the step of advancing a spacer and helical lock instrumentation assembly through an incision and into a predetermined position in an intervertebral space further comprises the step of abutting an engagement face on said spacer inserter against an outer wall of a bone.

19. The method of claim 1 wherein the step of advancing a spacer and helical lock instrumentation assembly through an incision and into a predetermined position in an intervertebral space further comprises the step of abutting a receded engagement face on said spacer inserter against an outer wall of a bone.

20. The method of claim 1 further comprising the step of reversing said locking rod to release said spacer inserter from said bone spacer.

* * * * *